(12) United States Patent
Agardh et al.

(10) Patent No.: US 11,166,993 B2
(45) Date of Patent: Nov. 9, 2021

(54) METHODS FOR CELIAC DISEASE USING LACTOBACILLUS STRAINS

(71) Applicant: Probi AB, Lund (SE)

(72) Inventors: Daniel Agardh, Lomma (SE); Irini Lazou Ahrén, Lund (SE); Lars Niklas Larsson, Lund (SE)

(73) Assignee: Probi AB, Lund (SE)

( * ) Notice: Subject to any disclaimer, the term of this patent is extended or adjusted under 35 U.S.C. 154(b) by 165 days.

(21) Appl. No.: 16/477,259

(22) PCT Filed: Jan. 12, 2018

(86) PCT No.: PCT/EP2018/050789
§ 371 (c)(1),
(2) Date: Jul. 11, 2019

(87) PCT Pub. No.: WO2018/130667
PCT Pub. Date: Jul. 19, 2018

(65) Prior Publication Data
US 2019/0358275 A1 Nov. 28, 2019

(30) Foreign Application Priority Data

Jan. 12, 2017 (GB) ..................................... 1700542
Jun. 19, 2017 (GB) ..................................... 1709731

(51) Int. Cl.
*A61K 35/747* (2015.01)
*A61K 9/00* (2006.01)
*A61K 35/74* (2015.01)

(52) U.S. Cl.
CPC .......... *A61K 35/747* (2013.01); *A61K 9/0053* (2013.01); *A61K 35/74* (2013.01)

(58) Field of Classification Search
CPC .... A61K 35/747; A61K 35/74; A61K 9/0053; A61K 36/185; A61K 9/14; A61K 9/48; A61K 9/19; A61K 31/593; A61P 37/00; A61P 17/00; A61P 1/00; A61P 1/04; A61P 1/10; A61P 1/14; A61P 29/00; A61P 35/00; A61P 37/08; A61P 3/10; A61P 19/10; A23L 19/01; Y02A 50/30; Y02A 50/481; C12N 15/01; C12N 1/20; C12N 9/0067; C12N 9/1217; C12N 9/88; C12N 9/90; C12Y 102/01012; C12Y 207/02003; C12Y 402/01011; C12Y 503/01001; C12R 1/23
See application file for complete search history.

(56) References Cited

U.S. PATENT DOCUMENTS

2011/0293644 A1  12/2011  Anderson et al.

FOREIGN PATENT DOCUMENTS

| WO | WO-2004076615 A2 * | 9/2004 | ..... C12Y 102/01012 |
|---|---|---|---|
| WO | 2007/040444 A1 | 4/2007 | |
| WO | 2007/108763 A1 | 9/2007 | |
| WO | 2007/108764 A2 | 9/2007 | |
| WO | 2013/192163 A1 | 12/2013 | |

OTHER PUBLICATIONS

Van Der Windt et al., Diagnostic testing for celiac disease among patients with abdominal symptoms: a systematic review. JAMA. May 5, 2010;303(17):1738-46.
Wierdsma et al., Vitamin and mineral deficiencies are highly prevalent in newly diagnosed celiac disease patients. Nutrients. Sep. 30, 2013;5(10):3975-92.
International Search Report and Written Opinion for PCTEP2018050789, dated Apr. 13, 2018, 11 pages.
Agardh et al., Prediction of silent celiac disease at diagnosis of childhood type 1 diabetes by tissue transglutaminase autoantibodies and HLA. Pediatr Diabetes. Jun. 2001;2(2):58-65.
Agardh et al., Reduction of tissue transglutaminase autoantibody levels by gluten-free diet is associated with changes in subsets of peripheral blood lymphocytes in children with newly diagnosed coeliac disease. Clin Exp Immunol. Apr. 2006;144(1):67-75.
Agardh et al., Using radioligand-binding assays to measure tissue transglutaminase autoantibodies in young children. Acta Paediatr. Aug. 2004;93(8):1046-51.
Agardh, Can gluten intolerance be prevented with probiotics? Crafoord's Science Lunch at Martas Café, City Library in Lund. Youtube video, retrieved online at: <https://www.youtube.com/watch?v=1S>. 1 page, Mar. 15, 2017 (Swedish).
Bannister et al., Can celiac serology alone be used as a marker of duodenal mucosal recovery in children with celiac disease on a gluten-free diet? Am J Gastroenterol. Sep. 2014;109(9):1478-83.
Caruso et al., Appropriate nutrient supplementation in celiac disease. Ann Med. Dec. 2013;45(8):522-31.
Celiac Disease Awareness Campaign. Provider Points, Testing for Celiac Disease, www.celiac.nih.gov, 2 pages, (2013).
Celiac Disease Foundation. Screening. celiac.org, 3 pages, (1998-2017).
D'Arienzo et al., Immunomodulatory effects of lactobacillus casei administration in a mouse model of gliadin-sensitive enteropathy. Scand J Immunol. Oct. 2011;74(4):335-41.
Dallagnol et al., Fermentation of quinoa and wheat slurries by lactobacillus plantarum CRL 778: proteolytic activity. Appl Microbiol Biotechnol. Apr. 2013,97(7):3129-40.
De Angelis et al., VSL#3 probiotic preparation has the capacity to hydrolyze gliadin polypeptides responsible for celiac sprue. Biochim Biophys Acta. Jan. 2006;1762(1):80-93.

(Continued)

*Primary Examiner* — Deborah K Ware
(74) *Attorney, Agent, or Firm* — McCarter & English, LLP; Yu Lu

(57) ABSTRACT

The present invention relates to at least one probiotic strain of *Lactobacillus* for use in a subject for the prevention and/or treatment of celiac disease autoimmunity (CDA), or for use in the prevention and/or treatment of celiac disease (CD).
A preferred composition for use according to the invention is a composition comprising a combination of *Lactobacillus paracasei* and *Lactobacillus plantarum*, especially *L. paracasei* 8700:2 (DSM 13434) in combination with *L. plantarum* HEAL 9 (DSM 15312).

12 Claims, 2 Drawing Sheets

(56) References Cited

OTHER PUBLICATIONS

De Palma et al., Pivotal advance: bifidobacteria and gram-negative bacteria differentially influence immune responses in the proinflammatory milieu of celiac disease. J Leukoc Biol. May 2010;87(5):765-78.
Dunne et al., Persistent Changes in Circulating and Intestinal gamma delta T Cell Subsets, Invariant Natural Killer T Cells and Mucosal-Associated Invariant T Cells in Children and Adults With Coeliac Disease. PLoS One. Oct. 4, 2013;8(10):e76008.
Erdem et al., Vitamin and mineral deficiency in children newly diagnosed with celiac disease. Turk J Med Sci. 2015;45(4):833-6.
Fasano et al., Genetics of Celiac Disease. Medscape. Retrieved online at: http://emedicine.medscape.com/article/1790189-overview. 7 pages, (2016).
Frisullo et al., Increased CD4+CD25+Foxp3+ T cells in peripheral blood of celiac disease patients: correlation with dietary treatment. Hum Immunol. Jun. 2009;70(6):430-5.
Hakansson et al., Effects of lactobacillus plantarum and lactobacillus paracasei on the peripheral immune response in children with celiac disease autoimmunity: a randomized, double-blind, placebo-controlled clinical trial. Nutrients. Aug. 16, 2019;11(8):1925. 12 pages.
Hakansson et al., Lactobacillus plantarum Heal9 and lactobacilius paracasei 8700:2 suppress ongoing celiac autoimmunity in children at genetic risk for developing celiac disease. 17th International Celiac Disease Symposium. 1 Page, (2017).
Hakansson et al., Lactobacilius plantarum Heal9 and lactobacilius paracasei 8700:2 suppress ongoing celiac autoimmunity in children at genetic risk for developing celiac disease. 17th International Celiac Disease Symposium. Poster Presentation PI37, pp. 084-085, (2017).
Hakansson, Lactobacillus plantarum Heal9 and lactobacilius paracasei 8700:2 suppress ongoing celiac autoimmunity in children at genetic risk for developing celiac disease. Medicon Valley Alliance Microbiome Summit 2017. Slideshow, 13 pages, (2017).
Hansson, Can probiotics affect the immunological activity in celiac disease autoimmunity? Master Thesis, Lunds Universitet. 18 pages, (2017).
Hunt et al., Novel celiac disease genetic determinants related to the immune response. Nat Genet. Apr. 2008;40(4):395-402.
Husby et al., European society for pediatric gastroenterology, hepatology, and nutrition guidelines for the diagnosis of coeliac disease. J Pediatr Gastroenterol Nutr. Jan. 2012;54(1):136-60.
Iellem et al., Skin-versus gut-skewed homing receptor expression and intrinsic CCR4 expression on human peripheral blood CD4+ CD25+ suppressor T cells. Eur J Immunol. Jun. 2003;33(6):1488-96.
Kerttula et al., Circulating T lymphocyte subsets in coeliac disease (CoD) patients and healthy family members. Clin Exp Immunol. Mar. 1998;111(3):536-40.
Laparra et al., Bifidobacteria inhibit the inflammatory response induced by gliadins in intestinal epithelial cells via modifications of toxic peptide generation during digestion. J Cell Biochem. Mar. 1, 2010;109(4):801-7.
Lavasani et al., A novel probiotic mixture exerts a therapeutic effect on experimental autoimmune encephalomyelitis mediated by IL-10 producing regulatory T cells. PLos One. Feb. 2, 2010;5(2):e9009, 11 pages.
Liu et al., Risk of pediatric celiac disease according to HLA haplotype and country. N Engl J Med. Jul. 3, 2014;371(1):42-9.
Londei et al., Gliadin as a stimulator of innate responses in celiac disease. Mol Immunol. May 2005;42(8):913-8.
Ludvigsson et al., Clinical management of coeliac disease. J Intern Med. Jun. 2011;269(6):560-71.
Mayo Clinic. Celiac Disease, Diagnosis. Retrieved online at: https://www.mayoclinic.org/diseases-conditions/celiac-disease/diagnosis-treatment/drc-20352225. 1 page, (2017).
Mayo Clinic. Celiac Disease, Symptoms and Causes. Retrieved online at: https://www.mayoclinic.org/diseases-conditions/celiac-disease/symptoms-causes/syc-20352220. 4 pages, (2017).
Medicon Valley Alliance Microbiome Summit Program Outline. Retrieved online at: http://mva.org/networks/medicon-valley-alliance-microbiome-network/microbiome-summit-2017/program-2/. 4 pages, Oct. 2017.
Midhagen et al., Antibody levels in adult patients with coeliac disease during gluten-free diet: a rapid initial decrease of clinical importance. J Intern Med. Dec. 2004;256(6):519-24.
Montelius. Could probiotics delay the onset of gluten intolerance? Probi AB. Slideshow, 23 pages, (2018).
Nadal et al., Imbalance in the composition of the duodenal microbiota of children with coeliac disease. J Med Microbiol. Dec. 2007;56(Pt 12):1669-1674.
Olivares et al., Double-blind, randomised, placebo-controlled intervention trial to evaluate the effects of bifidobacterium longum CECT 7347 in children with newly diagnosed coeliac disease. Br J Nutr. Jul. 14, 2014;112(1):30-40.
Pisarello et al., Decrease in lactobacilli in the intestinal microbiota of celiac children with a gluten-free diet, and selection of potentially probiotic strains. Can J Microbiol 2015;61:32-7.
Pozo-Rubio et al., Immune development and intestinal microbiota in celiac disease. Clin Dev Immunol. 2012;2012:654143.
Reinton et al., A one-step real-time PCR assay for detection of DQA1*05, DQB1*02 and DQB1*0302 to aid diagnosis of celiac disease. J Immunol Methods. Oct. 20, 2006;316(1-2):125-32.
Sacchetti et al., Rapid identification of HLA DQA1*0501, DQB1*0201 and DRB1*04 alleles in celiac disease by a PCR based methodology. Clin Chem. Nov. 1997;43(11):2204-6.
Sarno et al., Lactobacillus paracasei CBA L74 interferes with gliadin peptides entrance in caco-2 cells. Int J Food Sci Nutr. Dec. 2014;65(8):953-9.
Schosler et al., Symptoms and findings in adult-onset celiac disease in a historical danish patient cohort. Scand J Gastroenterol. Mar. 2016;51(3):288-94.
Schuppan et al., Celiac disease: from pathogenesis to novel therapies. Gastroenterology. Dec. 2009;137(6):1912-33.
Selleski et al., Simplifying celiac disease predisposing HLA-DQ alleles determination by the real time PCR method. Arq Gastroenterol. Apr.-Jun. 2015;52(2):143-6.
Smecuol et al., Exploratory, randomized, double-blind, placebo-controlled study on the effects of bifidobacterium infantis natren life start strain super strain in active celiac disease. J Clin Gastroenterol. Feb. 2013;47(2):139-47.
Smyth et al., Shared and distinct genetic variants in type 1 diabetes and celiac disease. N Eng J Med. Dec. 25, 2008;359(26):2767-77.
Sollid et al., Evidence for a primary association of celiac disease to a particular HLA-DQ alpha/beta heterodimer. J Exp Med. Jan. 1, 1989;169(1):345-50.
Teddy Study Group. The environmental determinants of diabetes in the young (Teddy) study: study design. Pediatr Diabetes. Oct. 2007;8(5):286-98.
Tiitanen et al., Infiltration of forkhead box P3-expressing cells in small intestinal mucosa in coeliac disease but not in type 1 diabetes. Clin Exp Immunol. Jun. 2008;152(3):498-507.
Song et al., Characterization of Selected Lactobacillus Strains for Use as Probiotics. Korean J Food Sci Anim Resour. 2015;35(4):551-6.

* cited by examiner

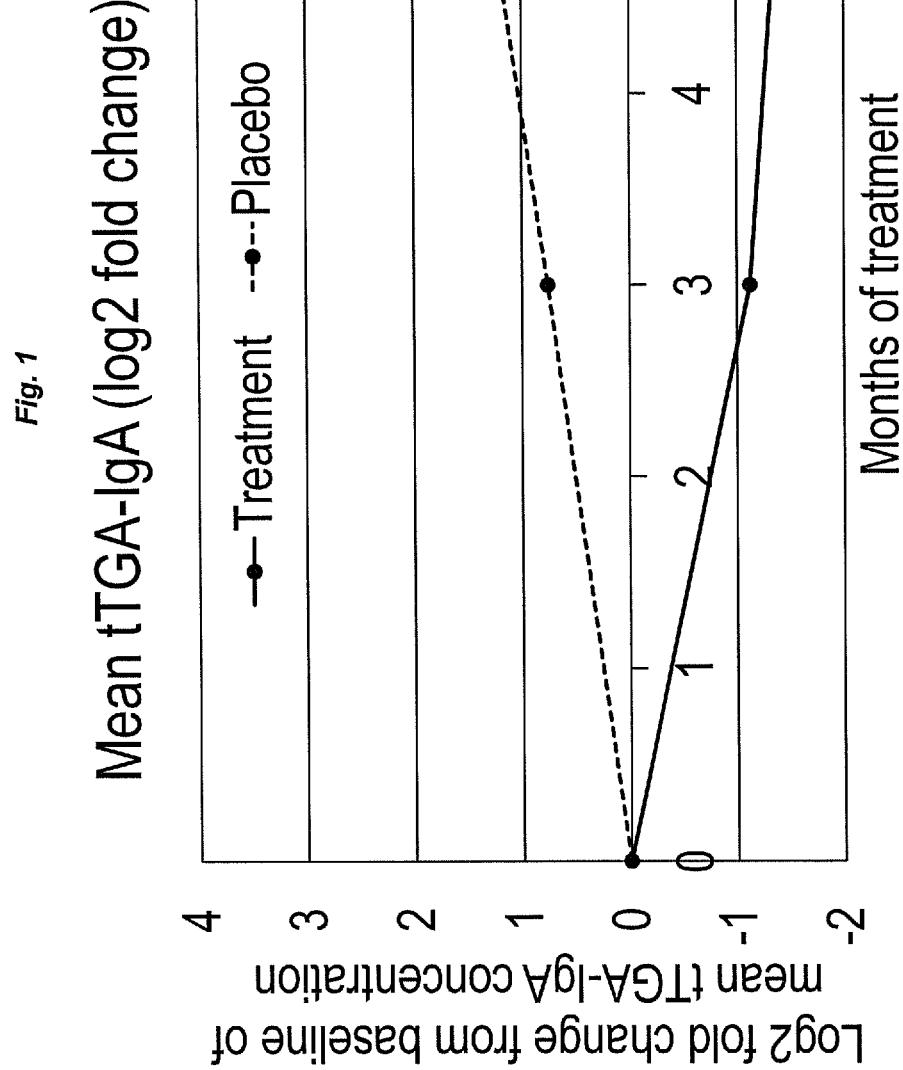

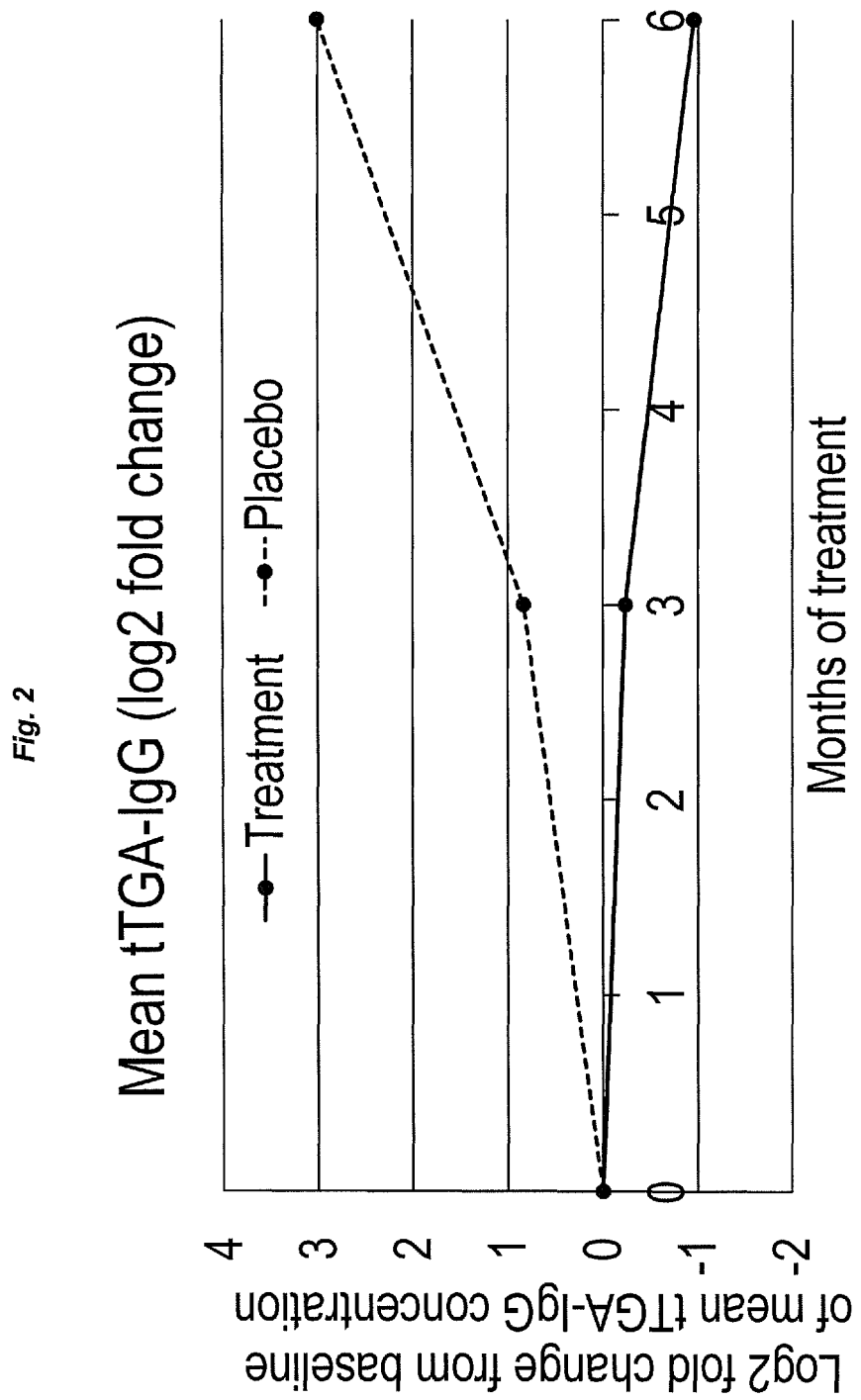

METHODS FOR CELIAC DISEASE USING LACTOBACILLUS STRAINS

REFERENCE TO RELATED APPLICATIONS

This is a U.S. National Stage Application filed under 35 U.S.C. § 371(c), based on International Patent Application No. PCT/EP2018/050789, filed on Jan. 12, 2018, published in English on Jul. 19, 2018 as WO 2018/130667 A1, which claims priority to GB 1700542.2, filed on Jan. 12, 2017, and GB 1709731.2, filed on Jun. 19, 2017, the entire contents of the above referenced applications, including drawings and any sequence listing, are incorporated herein by reference in their entirety.

The present invention relates to at least one probiotic strain of a *Lactobacillus* species for use in the prevention and/or treatment in a subject of celiac disease autoimmunity (CDA), or celiac disease (CD).

The invention also provides compositions for such uses and methods of preventing and/or treating CDA and/or CD involving administering an effective amount of said probiotic strain to a subject.

INTRODUCTION

Celiac disease (CD) is a chronic immune-mediated disorder affecting the intestinal mucosa of the small bowel. It is caused by intolerance to gluten, the major storage protein found in wheat, rye and barley (Schuppan D, et al. *Gastroenterology.* 2009; 137(6):1912-33). Classical symptoms and clinical signs of celiac disease include abdominal discomfort, distention and diarrhoea, followed by signs of malnutrition (e.g., weight loss, anemia and osteoporosis). However, a significant portion of patients lack symptoms and are diagnosed through screening (Ludvigsson J F, et al. *Journal of Internal Medicine.* 2011; 269(6):560-71). Currently, treatment consists of a life-long gluten free diet (GFD).

The pathophysiology of CD is not completely understood but is proposed to be T-cell driven. Following the digestion of gluten proteins in the small bowel, the resulting gliadin peptides somehow cross the epithelial barrier and are presented by antigen-presenting cells on MHC-II-structures, enabling the activation of gliadin-specific CD4+ T-helper ($T_H$) 1 cells and CD8+ cytotoxic T ($T_C$) cells in the lamina propria. This results in upregulation of several cytokines, IFN-γ, TNF-α and IL-21 in particular, of which the former two causes the typical mucosal remodeling and villous atrophy through activation of myelofibroblasts while the latter is likely involved in maintaining the activity of the CD4+ cells (Schuppan D, et al., supra). In the last decade, concomitant, direct stimulation of the innate immune system by gliadins has been shown to be an additional important factor in the development of disease. This is currently attributed to upregulation of IL-15 signaling in dendritic cells and macrophages, causing mucosal damage through activation of intra-epithelial lymphocytes (IELs) (Londei M, et al., *Molecular Immunology.* 2005; 42(8):913-8).

The global prevalence of CD is roughly estimated at 1%, but varies greatly between ethnic groups and geographic location. Sweden ranks amongst the most heavily afflicted nations with an estimated prevalence of 1.5-3% (Ludvigsson J F, et al., supra). It is yet to be fully determined what processes help induce this dysfunctional reaction to the gliadin structures, and why disease prevalence varies between populations. There is a clear genetic component in CD as evidenced by the fact that almost all celiac patients are carriers of the DR3-DQ2 and/or the DR4-DQ8 haplotypes (Sollid L M, et al. *The Journal of Experimental Medicine.* 1989; 169(1):345-50). In addition, a number of other less influential genes have also been found to affect the risk of disease, most of them related to the activation of the adaptive immune response (Hunt K A, et al., *Nature Genetics.* 2008; 40(4):395-402). CD shares these genetic risk traits with several other autoimmune disorders, most importantly type 1 diabetes (T1D), which shares its major susceptibility genes in the HLA-DQB1 and HLA-DRB1 loci as well as several non-HLA loci (Smyth D J, et al., *New England Journal of Medicine.* 2008; 359(26):2767-77). Nevertheless, genetics alone cannot explain CD, since only a small minority of those carrying these haplotypes develop the disease. The rapidly increasing incidence observed in many countries during the last decades also point to environmental factors contributing to the pathogenesis in some way. Important areas of investigation include infant feeding practices, breast milk feeding, (and variations or disturbances in the gut microbiota (De Palma G, et al., Advance: Bifidobacteria and Gram-negative bacteria differentially influence immune responses in the proinflammatory milieu of celiac disease. *Journal of Leukocyte Biology.* 2010; 87(5):765-78).

While intestinal biopsy was previously considered the gold standard for the diagnosis of CD, several serological markers have been discovered of which tissue transglutaminase autoantibodies (tTGA) are currently the most common in clinical practice due to its high diagnostic sensitivity and specificity (van der Windt D A, et al., Diagnostic testing for celiac disease among patients with abdominal symptoms: a systematic review. Jama. 2010; 303(17):1738-46). Furthermore, the revised guidelines from European Society for Paediatric Gastroenterology, Hepatology and Nutrition (ES-PGHAN) in 2012 (Husby S, et al., ESPGHAN guidelines for the diagnosis of coeliac disease. *Journal of Pediatric Gastroenterology and Nutrition.* 2012; 54(1):136-60) suggest that significantly elevated tTGA levels, if followed by appropriate further testing, may eliminate the need for biopsy to confirm the diagnosis. In the majority of CD patients, tTGA levels decrease after introduction of GFD.

In children, such a decrease is also highly predictive of histological improvement in the gut mucosa (Bannister E G, et al., *American Journal of Gastroenterology.* 2014; 109(9): 1478-83), indicating that tTGA may be used not only as a binary diagnostic tool but also as a marker for disease activity and dietary compliance. However, this brings the question of how to manage asymptomatic patients who are found to have persistently elevated tTGA levels, so called CD autoimmunity (CDA), or more widely referred to as potential CD if confirmed with normal intestinal biopsy features. These children are at increased risk of developing CD (Liu E, et al., *The New England Journal of Medicine.* 2014; 371(1):42-9), with no treatment options currently available to reduce or eliminate that risk other than a GFD.

BACKGROUND

Earlier studies have shown that the microbiota of patients with active CD is composed to a greater degree of gram-negative pathogens compared to healthy controls and symptom-free patients (Nadal I, et al., Imbalance in the composition of the duodenal microbiota of children with coeliac disease. *Journal of Medical Microbiology.* 2007; 56(Pt12): 1669-74). Accordingly, later studies have suggested that such a microbiota potentiates a higher degree of inflammatory reaction in response to gliadins (De Palma G, et al., Advance: Bifidobacteria and Gram-negative bacteria differentially influence immune responses in the proinflammatory milieu of celiac disease. *Journal of Leukocyte Biology.* 2010; 87(5):765-78) and conversely, that certain *Bifidobacterium* strains influence the digestion of gliadins and reduces their immunological potential (Laparra J M, et al., Bifidobacteria inhibit the inflammatory response induced by gliadins in intestinal epithelial cells via modifications of toxic peptide generation during digestion. *Journal of Cellular Biochemistry.* 2010; 109(4):801-7).

Some recently published studies have examined the effect of administering specific *Bifidobacterium* strains in the context of already clinically manifested CD. Olivares et al. (Olivares M, et al., *The British Journal of Nutrition.* 2014; 112(1):30-40) randomized 36 children recently diagnosed with CD to treatment with either daily consumption of *Bifidobacterium longum* CECT 7347 or placebo for 3 months, in addition to GFD. Due to introduction of GFD, the probiotic effect on immunologic parameters is difficult to appreciate; the study did not examine tTGA levels, but did find a significant decrease in total levels of mature T cells in the treatment group compared to placebo. In addition, they showed that children in the probiotic-treated group achieved a greater height percentage gain compare with controls.

Also, Smecuol et al. *Journal of Clinical Gastroenterology.* 2013; 47(2):139-47) treated 22 adult CD patients currently not on GFD with *Bifidobacterium infantis* or placebo daily for 3 weeks and evaluated intestinal permeability, immunological parameters, and changes in symptoms. Participants in the probiotic-treated group reported improvement of gastrointestinal symptoms compared to controls. However, unlike *B. longum* CECT 7347, *B. infantis* (NLS) failed to influence inflammatory markers and the gut microbiota and host-related defense mechanisms.

Whilst both of the above studies with specific *Bifidobacterium* strains suggest some beneficial role for those *Bifidobacterium* strains in CD, they also highlight the need for further studies.

Thus, despite significant investigations of CDA and CD, currently the only available treatment for CD is a gluten free diet (GFD). Hence, there is a need for compositions and methods for preventing and/or treating celiac disease autoimmunity (CDA), or for preventing and/or treating celiac disease (CD).

STATEMENT OF INVENTION

According to the invention there is provided at least one probiotic strain of a *Lactobacillus* species for use in a subject for the prevention and/or treatment of celiac disease autoimmunity (CDA), or for the prevention and/or treatment of celiac disease (CD).

By "use for the prevention and/or treatment" we mean a use which gives rise to an effect in a subject of preventing, delaying, reducing the severity and/or removing one or more symptoms and/or other markers associated with CDA or CD.

Probiotic *Lactobacillus* Strains

A preferred probiotic strain of a *Lactobacillus* species is selected from: *L. paracasei; L. plantarum; L. acidophilus; L. rhamnosus; L. casei; L. reuteri; L. brevis; L. crispatus; L. bulgaricus; L. fermentum; L. salivarius; L. johnsonii;* and *L. lactis*

Preferably, the at least one probiotic strain of a *Lactobacillus* species is *Lactobacillus paracasei* and/or *Lactobacillus plantarum*.

*Lactobacillus* Strain Deposits

Preferred strains of Lactobacilli for use in accordance with the present invention have been deposited under the Budapest Treaty by Probi A. B., Sölvegatan 41, Lund 22370, Sweden, as follows:—

| Species | Strain | Accession No. | Date of deposit | Depositor | Depositary |
|---|---|---|---|---|---|
| *Lactobacillus plantarum* | HEAL 9 | DSM 15312 | 27 Nov. 2002 | Probi | DSMZ |
| | HEAL 19 | DSM 15313 | 27 Nov. 2002 | Probi | DSMZ |
| | HEAL 99 | DSM 15316 | 27 Nov. 2002 | Probi | DSMZ |
| | 299 | DSM 6595 | 2 Jul. 1991 | Probi | DSMZ |
| | 299v | DSM 9843 | 16 Mar. 1995 | Probi | DSMZ |
| | GOS42 | DSM 32131 | 2 Sep. 2015 | Probi | DSMZ |
| *Lactobacillus paracasei* | 8700:2 | DSM 13434 | 6 Apr. 2000 | Probi | DSMZ |
| | O2A | DSM 13432 | 6 Apr. 2000 | Probi | DSMZ |
| *Lactobacillus rhamnosus* | 271 | DSM 6594 | 2 Jul. 1991 | Probi | DSMZ |

Preferably, the strain of *L. paracasei* is selected from one or more of *L. paracasei* 8700:2 (DSM 13434) *L. paracasei* 02:A (DSM 13432).

Preferably, the strain of *L. plantarum* is selected from one or more of *L. plantarum* HEAL 9 (DSM 15312); *L. plantarum* HEAL 19 (DSM 15313); *L. plantarum* HEAL 99 (DSM 15316); *L. plantarum* 299v (DSM 9843); and/or *L. plantarum* 299 (DSM 6595).

Advantageously, the invention provides a combination of at least one probiotic *L. paracasei* strain and at least one probiotic *L. plantarum* strain for use in a subject for the prevention and/or treatment of celiac disease autoimmunity (CDA), or for the prevention and/or treatment of celiac disease (CD).

Most preferably, the combination is *L. paracasei* 8700:2 (DSM 13434) and *L. plantarum* HEAL 9 (DSM 15312).

The compositions may comprise the specified probiotic strain or strains of Lactobacilli, but preferably they consist of the specified strains without another effective amount of any other probiotic strains of Lactobacilli or other microorganisms.

Compositions and Formulations

The probiotic strains of the invention are preferably freeze-dried.

The probiotic strains of the invention may be provided together with a suitable carrier, diluent or excipient as a solid or liquid formulation, which may be a pharmaceutical formulation in on embodiment.

Examples of a suitable liquid carrier include water and other aqueous solvents.

Examples of a suitable solid carrier include maltodextrin, inulin, potato starch, corn starch or other vegetable starch, microcrystalline cellulose (MCC), and sugar alcohols.

The composition may be a dry fermented or non-fermented composition. In the case of a dry non-fermented composition, fermentation takes place in the gastrointestinal tract after ingestion of the composition by a subject.

In use, the probiotic strain(s) of the invention may be mixed with a liquid or solid carrier before administration to a subject. For example, the subject may mix the strain(s) with a carrier consisting of water or some other aqueous solvent, or a drink prior to intake. Similarly, the probiotic strains may be mixed with a carrier consisting of one or more foods. Preferred foods are gluten free products such as fermented or non-fermented dairy products such as yoghurts, fruit juices; beverages, soups, plant based foods such as soy products, dry food bars, baby food, infant nutrition, infant formula, breast milk replacements from birth.

Infant or baby formula milk is a particularly preferred carrier for the probiotic of Lactobacilli strain(s) of the invention. It may be in a dry powder form for mixing with water before feeding it to babies as a ready-to-feed liquid form. It is normally made from cows' milk and contains whey and casein protein.

The probiotic strain(s) of the invention may also be provided in a composition together with one or more ingredients of known dietary supplements, for example, micronutrients such as vitamins and minerals.

Classical symptoms and clinical signs of celiac disease include abdominal discomfort, distention and diarrhea, followed by signs of malnutrition (e.g., weight loss, anemia and osteoporosis). Considering the risks involved with malnutrition, it has been published that children newly diagnosed with celiac disease were deficient in vitamin D, zinc and iron (Erdem et al., Vitamin and mineral deficiency in children newly diagnosed with celiac disease. *Turk J Med Sci.* 2015; 45(4):833-6 2015). Similarly, adults with newly diagnosed celiac disease and untreated CD patients were also found to have values below the limits of reference for vitamins $B_6$ and $B_{12}$, vitamin D, folic acid, zinc, magnesium and iron (Wierdsma et al., Vitamin and mineral deficiencies are highly prevalent in newly diagnosed celiac disease patients. *Nutrients.* 2013 Sep. 30; 5(10):3975-92. doi: 10.3390/nu5103975, Caruso et al., Appropriate nutrient supplementation in celiac disease 2013 *Ann Med.* 2013 December; 45(8):522-31. doi: 10.3109/07853890.2013.849383. Review, Schøsler et al., Symptoms and findings in adult-onset celiac disease in a historical Danish patient cohort *Scandinavian Journal of Gastroenterology* Vol. 51, ISS. 3, 2016). In most of the cases the removal of gluten from the diet, once a person has been diagnosed with CD or CDA, restores the "healthy" histology of the gut and leads to normalization of the vitamin and mineral status. However, resolution of mucosal inflammation by adapting to a gluten free diet is not always enough to counteract mineral deficiency (Caruso et al. 2013 supra). Hence, supplementation of people diagnosed with CD/CDA or at risk of developing CD/CDA with vitamins and/or minerals may be used together with the probiotic Lactobacilli according to the invention. Preferably, the vitamin(s) and/or mineral(s) are selected from one or more of the vitamins: A, $B_6$, $B_{12}$, D; and/or the minerals: iron, zinc, magnesium.

Preferably, the probiotic strain(s) compositions the invention are provided in the form of a capsule or tablet or a powder for oral administration. Stick packs are a popular type of single-portion/single dose packaging used in the food industry and the pharmaceutical sector (see www.selo.com/packaging-machines/stick-packs/). They are very convenient for consumers to use and by containing a predetermined amount of the probiotic compositions of the invention, ensure the correct dose is taken to achieve a desired preventative and/or therapeutic effect according to the invention.

Preferably, in use the probiotic strain(s) of the invention are administered to a subject in a daily amount of from $1\times10^6$ to $1\times10^{14}$ colony forming units (CFU), preferably from $1\times10^9$ to $1\times10^{11}$ CFU and most preferably $1\times10^{10}$ CFU. The daily amount of CFU is preferably administered in a single dose or serving.

Subjects to be Treated

Preferably, the subject is a human. Advantageously, the human subject is a child. Preferably the child is less than 18, 17, 16, 15, 14, 13, 12, 11, 10, 9, 8, 7, 6, 5, 4, 3, 2, or 1 years old. Advantageously, the compositions of the invention are for administration from birth and especially from weaning, i.e. the point at which the baby ceases to be fed entirely by breast milk.

Identification of At-Risk Subjects

Preferably the subject lacks one or more of the symptoms of CD but is at an increased risk of developing CD.

Ideally, the subject is identified as being at an increased risk of CD by the presence of one or more serological, immunological and/or genetic risk factors.

A variety of methods for detecting the presence of serological, immunological and/or genetic risk factors are well known to skilled persons; but examples of particularly suitable methods are provided herein for convenience.

CDA and/or CD-Associated Markers

Serotyping
DQ2 positive
DQ8 positive

Genetic testing
DQ2.5$_{cis}$ haplotype (DQA1*05/DQB1*02)
DQ2.2$_{cis}$ haplotype (DQA1*02:01/DQB1*02:02)
DQ2.5$_{trans}$ haplotype, e.g. DQ2.2$_{cis}$ haplotype (DQA1*02:01/DQB1*02:02) with DQ7.5$_{cis}$ haplotype (DQA1*05:05/DQB1*03:01)
DQ8$_{cis}$ haplotype (DQA1*03/DQB1*03:02)
DQA1*05:01 allele
DQA1*05:05 allele
DQB1*03:02 allele Increased risk of developing celiac disease can be determined by immunological serotyping and/or genetic analysis. Immunological serotyping is used to identify the presence of the DQ2 serotype marker and/or the DQ8 serotype marker. Genetic analysis of genomic DNA can be performed by sequence-specific PCR using sequence-specific primers (PCR-SSP) or by gene sequencing. Sequence-specific PCR methods include: PCR with sequence-specific primers (PCR-SSP) (Sacchetti L, et al., Rapid Identification of HLA DQA1*0501, DQB1*0201, and DRB1*04 Alleles in Celiac Disease by a PCR-Based Methodology. *Clin Chem.* 1997 November; 43(11):2204-6); quantitative real-time PCR (qPCR) with sequence-specific primers and TaqMan probes (Reinton et al., A one-step real-time PCR assay for detection of DQA1*05, DQB1*02 and DQB1*0302 to aid diagnosis of celiac disease. *J Immunol Methods.* 2006 Oct. 20; 316 (1-2):125-32. Epub 2006 Sep. 18); qPCR with sequence-specific primers and melting curve analysis (Selleski et al., Simplifying celiac disease predisposing HLA-DQ alleles determination by the real time PCR method. *Arq Gastroenterol.* 2015 April-June; 52(2):143-6. doi: 10.1590/S0004-28032015000200013); PCR amplification followed by hybridization with sequence-specific oligonucleotides Gene sequencing methods include Sanger sequencing with chain-terminating dideoxynucleotides, pyrosequencing, sequencing by synthesis (Illumine sequencing), sequencing by ligation (SOLiD sequencing), nanopore sequencing (MinION), Ion Torrent semiconductor sequencing and single-molecule real-time sequencing (Pacific Biosciences).

Genetic markers corresponding to DQ2 or DQ8 serotypes include: DQ2.5$_{cis}$ haplotype (DQA1*05/DQB1*02); DQ2.2$_{cis}$ haplotype (DQA1*02:01/DQB1*02:02); DQ2.5$_{trans}$ haplotype, e.g. DQ2.2$_{cis}$ haplotype (DQA1*02:01/DQB1*02:02) with DQ7.5$_{cis}$ haplotype (DQA1*05:05/DQB1*03:01); DQ8$_{cis}$ haplotype (DQA1*03/DQB1*03:02); DQA1*05:01 allele; DQA1*05:05 allele; DQB1*03:02 allele.

Immunological markers for CDA and/or CD include: tissue transglutaminase antibody level, including by radioligand binding assays (Agardh et al., Using radioligand-binding assays to measure tissue transglutaminase autoantibodies in young children. Acta paediatrica (Oslo, Norway: 1992). 2004; 93(8):1046-51, Agardh et al., Prediction of silent celiac disease at diagnosis of childhood type 1 diabetes by tissue transglutaminase autoantibodies and HLA. Pediatric diabetes. 2001; 2(2):58-65); IgA Endomysial antibody (EMA) level, including in the absence of a deficiency in total serum IgA; deaminated gliadin peptide (DGP IgA and IgG) levels.

Preferably, the one or more risk factor(s) is HLA-DQ2 and/or HLA-DQ8.

Preferably, the one or more immunological risk factors is persistent tissue transglutaminase (tGA) positivity, i.e. a tGA positive test on two or more consecutive occasions.

tTG positivity can be shown by the presence of tTG autoantibodies, preferably IgA-tGA and/or IgG-tGA, as described herein.

BRIEF DESCRIPTION OF FIGURES

FIG. 1: shows the change in mean tTGA-IgA level over time in the *L. paracasei+L. plantarum* strain treatment group compared to the placebo group.

FIG. 2: shows the change in mean tTGA-IgG level over time in the *L. paracasei+L. plantarum* treatment group compared to placebo.

EXAMPLES

The following materials, methods and examples embody aspects of the present invention.

Materials and Methods

Study Population Identification of Subjects with an Increased Risk of CD by Genetic Serological and Immunological Risk Factors Participants were recruited from the CiPiS and Swedish participants of TEDDY study. The TEDDY study protocol has been thoroughly described elsewhere (The Environmental Determinants of Diabetes in the Young (TEDDY) study: study design. Pediatric Diabetes. 2007; 8(5):286-98). In short, between 2004 and 2010, newborns at these centers were HLA genotyped and considered eligible if carrying one of the following genotypes: DR3-DQ2/DR4-DQ8, DR4-DQ8/DR4-DQ8, DR4-DQ8/DR8, DR3-DQ2/DR3-DQ2, DR4-DQ8/DR4b, DR4-DQ8/DR1, DR4-DQ8/DR13, DR4-DQ8/DR9, or DR3-DQ2/DR9. At the Swedish center, a total of 48,140 children were screened of whom 3,723 were found to be HLA-eligible. Of these, written informed consent to study participation was provided by parents or primary caretakers in a total of 2,525 cases. Within the TEDDY protocol blood samples are collected every 6 months and children are annually screened for tTGA starting at 2 years of age. Upon showing tTGA positivity, earlier blood samples are analyzed retrospectively to determine the time of seroconversion. Participants testing positive in 2 consecutive blood samples are considered persistently tTGA positive, and ruled in for CDA. All definitive results are based on laboratory analysis performed in the European reference laboratory at Southmead Hospital, Bristol, United Kingdom. Further evaluation concerning CD is outside the scope of the TEDDY protocol. In Sweden, the decision to perform an intestinal biopsy is made on a case-by-case basis depending on tTGA levels, degree of symptoms and signs of malnutrition.

In the CiPiS study, children born in Skåne between 2000 and 2004 were screened using HLA genotyping of cord blood and a questionnaire concerning maternal factors. Children carrying DQ2 and/or DQ8 were considered at HLA risk. A total of 6202 children at risk were invited, as well as 7654 children lacking HLA risk as controls. tTGA screening was performed at age 3 in 1620/6206 (26.1%) of participants in the HLA-risk group and 1815/7654 (23.7%) of controls, and at age 9 in 1910/5870 (32.5%) of participants with HLA-risk and 2176 of 7072 (30.6%) of controls. If tested tTGA positive, participants were re-tested at least 3 months later to confirm persistent tTGA positivity, whereupon they were referred to the local pediatric clinic for an intestinal biopsy. Participants were continuously invited from these 2 cohorts between March 2012 and August 2015. Inclusion criteria were as follows:

tTGA positivity in 2 consecutive samples, <30 U/ml using the Bristol tTGA assay.

No diagnosis of celiac disease.

Negative in all diabetes-associated autoantibodies screened for in the TEDDY protocol (GADA, IAA, IA-2A, ZnT8A).

Not participating in the TEDDY study through a long-distance protocol.

Children positive in T1D-associated autoantibodies were excluded from the present study to minimize influences on the natural history of islet autoimmunity. However, it will be appreciated that T1D-associated autoantibodies constitute a serological marker for increased risk of developing CD and as such can be used to identify preferred subjects for preventative and/or therapeutic treatment according to the uses and methods of the present invention.

Study Design

Children matching the inclusion criteria were invited for an initial meeting, then scheduled for follow-up visits approximately 3 and 6 months later. Participants were randomized at a 1:1 ratio to treatment or control group. At the initial meeting and first follow-up visit, each group was provided with a powdered formulation containing Lactobacilli, or a placebo, respectively, and instructed to consume the product daily by ingestion of the powder after dissolution in 100 ml of cold liquid or after mixing with fruit/food, in association with a meal once daily, for a total period of 6 months, to halt consumption of any other food products containing probiotics, and to store the sachets refrigerated (2-8° C.). The parents were also instructed not to add the powder to hot drinks or hot food. At every visit, 10 ml venous blood and a fecal sample was collected. Allocation to the treatment or control group was blinded to participants, clinicians and lab personnel.

Tissue Transglutaminase Autoantibody Analysis—Immunological Risk Factor for Developing CD Radioligand binding assays (RBA) were used to assess tTGA as previously described (Agardh D, et al., Pediatric Diabetes. 2001; 2(2):58-65) (Agardh D et al., Using radioligand-binding assays to measure tissue transglutaminase autoantibodies in young children. Acta paediatrica (Oslo, Norway: 1992). 2004; 93(8):1046-51). In short, human tissue transglutaminase (tTG) was synthesized by in vitro transcription and translation of cDNA using the TNT SP6 Coupled Reticulocyte Lysate System (Promega, Madison, Wis., USA) in the presence of 35S-methionine (Perkin Elmer, Waltham, Mass., USA). Both IgG-tTGA and IgA-tTGA were analyzed. For IgG-tTGA analysis, 35S-tTG was diluted and added to human serum and incubated overnight at 4° C. Protein A sepharose (PAS) (Invitrogen, Thermo Fisher Scientific, Carlsbad, Calif., USA) was used to separate free and antibody-bound 35S-tTG by binding IgG in serum. PAS and immunoprecipitated 35S-tTG-serum were added to a 96 well MultiScreenHTS DV Filter Plate (Merck Life Science, Darmstadt, Germany) and incubated on a plate shaker, followed by washing. OptiPhase Supermix scintillation cocktail (Perkin Elmer) was added and reactivity was measured in a MicroBeta Counter TriLux (Perkin Elmer). IgA-tTGA analysis was performed similarly, except goat anti-human IgA-agarose (Merck Life Science) was used instead of PAS. The levels of TGA were expressed as U/mL calculated from standard curves containing approximately 2, 4, 8, 16, 31, 63, 125, 250, 500 and 1000 U/mL of respective IgA-tTGA and IgG-tTGA. The cut off level for positive values of IgG-tTG and IgA-tTG was set at >4.0 U/mL, which represented the $99^{th}$ percentile of 398 adult blood donors (Agardh D, et al., *Acta paediatrica*. 2004; 93(8): 1046-51). When selective IgA deficiency was suspected the participants were tested for total IgA levels as part of their original studies; however, no such condition was detected among the participants.

Lactobacilli Culture Preparation and Composition of Treatment Product

The lactobacilli culture was prepared by Probi A B, Lund, Sweden. Active product consisted of freeze-dried *L. paracasei* 8700:2 (DSM 13434) in combination with *L. plantarum* HEAL 9 (DSM 15312) with maltodextrin (Glucidex IT-19, Roquette, France) in the form of a powder containing a combined $1 \times 10^{10}$ CFU, with each strain being represented equally. Placebo consisted of powdered maltodextrin and yeast peptone (HYP-A, BioSpringer, France) to adjust colour and taste, so that the two test products (probiotic and placebo) were identical in appearance and taste. Participants were instructed to store the product in the refrigerator, and consume a one gram sachet of product every morning. It will be appreciated that it is the total CFU of *Lactobacillus* rather than the concentration (i.e. mass or number of *Lactobacillus* per unit of mass or volume of the composition) that is relevant to the efficacy of the product.

Flow Cytometry Analysis

Separation of Mononuclear Cells (PBMCs)

Peripheral blood mononuclear cells (PBMCs) from the cohorts in Example 1 were separated from whole blood by a density gradient centrifugation (1800 G) using a hydrophilic polysaccharide (BD Vac® CPT™ Cell Preparation Tube NC FICOLL™ 4 mL, Cat No 362760 Becton Dickinson, N.J., USA). Cells were separated within 2-24 hours after blood sample collection. The aspirated interphase mononuclear layer was washed three times with RPMI-1640 Medium with L-Glutamine (GIBCO no 21875034, Thermo Fisher Scientific, Gothenburg, Sweden). The cells were counted in an Abbott CELL_DYN Ruby to a final concentration of $1-4 \times 10^6$/mL Lymphocytes in RPMI-1640 (i.e. the volume of the PBMC suspension was adjusted so that there were $1-4 \times 10^6$ lymphocytes per mL).

Immunostaining Protocol

Summary

Following counting, PBMCs were stained with monoclonal antibodies directed to surface and intracellular structures. The monoclonal antibodies (Table 2) were pre-labelled with four fluorochromes, fluorescein isothiocyanate (FITC), Phycoerythrin (PE), Peridinin chlorophyll protein (PerCP) and Allophycocyanin (APC). Stained cells were analysed using a four-colour FACSCalibur® instrument (BD Biosciences, Calif., USA) by passing via a laser beam. The FACSCalibur® defines cell populations and count the cells by their characteristic features of size, granularity and fluorescence intensity. Optical detectors amplify and convert the light signals to electrical data signals. The data were acquired and analyzed in CellQuestPro® software (BD Biosciences).

TABLE 1

Antibodies used in flow cytometry analysis.

| Antibody & fluorochrome | Supplier | Catalogue No |
|---|---|---|
| CCR9 APC | R&D Systems, Inc., Abingdon, UK | FAB17991A |
| CD45RO APC | BD Biosciences, CA USA | 559865 |
| CD62L APC | BD Biosciences, CA USA | 559772 |
| IgG1 isotype APC | BD Biosciences, CA USA | 555751 |
| CD25 FITC | BD Biosciences, CA USA | 555431 |
| CD3 FITC | BD Biosciences, CA USA | 555332 |
| CD38 FITC | BD Biosciences, CA USA | 340909 |
| CCR4 PE | BD Biosciences, CA USA | 551120 |
| CD8 PE | BD Biosciences, CA USA | 345773 |
| CD45RA PE | BD Biosciences, CA USA | 555489 |
| Integrin beta7 PE | BD Biosciences, CA USA | 555945 |
| CD19 PerCP | BD Biosciences, CA USA | 345778 |
| CD4 PerCP | BD Biosciences, CA USA | 345770 |
| CD8 PerCP | BD Biosciences, CA USA | 345774 |
| CD3 FITC/CD16 + CD56 PE | BD Biosciences, CA USA | 342403 |
| IgG2a isotype FITC/IgG1 isotype PE/CD4 PerCP-Cy 5.5 | BD Biosciences, CA USA | 340965 |
| Human IgG Isotype Control | Fisher Scientific, Gothenburg, Sweden | 12000C |
| eBioscience ™ Human Regulatory T Cell Staining Kit (CD4, CD25, FoxP3) | AH diagnostics AB, Solna, Sweden | 88-8999-40 |

TABLE 2

Antibody combinations and concentrations used in flow cytometry analysis.

| | | | Direct Staining | | |
|---|---|---|---|---|---|
| Tube | Mixture Panel | Label | Mab prep in 100 µL | Dilution | Number of lymphocytes acquired, collected and gated |
| 1 | Isotype control | FITC/PE/PerCP | 5 µL | 1/20 | 3000 |
| | | APC | 2.5 µL | 1/40 | |
| 2 | CD3 | FITC | 5 µL | 1/20 | 10000 |
| | CD16 + 56 | PE | 5 µL | 1/5 | |
| | CD19 | PerCP | 20 µL | | |

TABLE 2-continued

Antibody combinations and concentrations used in flow cytometry analysis.

| | | | | | |
|---|---|---|---|---|---|
| 3 | CD3 | FITC | 5 μL | 1/20 | 10000 |
| | CD45RA | PE | 0.4 μL | 1/250 | |
| | CD4 | PerCP | 5 μL | 1/20 | |
| | CD45RO | APC | 20 μL | 1/5 | |
| 4 | CD3 | FITC | 5 μL | 1/20 | 10000 |
| | CD45RA | PE | 0.4 μL | 1/250 | |
| | CD8 | PerCP | 2.5 μL | 1/40 | |
| | CD45RO | APC | 20 μL | 1/5 | |
| 5 | CD3 | FITC | 5 μL | 1/20 | 10000 |
| | CD8 | PE | 0.4 μL | 1/250 | |
| | CD4 | PerCP | 5 μL | 1/20 | |
| | CD62L | APC | 2.5 μL | 1/40 | |
| 6 | CD25 | FITC | 10 μL | 1/10 | 100000 |
| | CD45RA | PE | 0.4 μL | 1/250 | |
| | CD4 | PerCP | 5 μL | 1/20 | |
| | CD45RO | APC | 20 μL | 1/5 | |
| 7 | CD25 | FITC | 10 μL | 1/10 | 50000 |
| | CCR4 | PE | 2.5 μL | 1/40 | |
| | CD4 | PerCP | 5 μL | 1/20 | |
| | CD45RO | APC | 20 μL | 1/5 | |
| 8 | CD25 | FITC | 10 μL | 1/10 | 50000 |
| | CCR4 | PE | 2.5 μL | 1/40 | |
| | CD4 | PerCP | 5 μL | 1/20 | |
| | CD62L | APC | 2.5 μL | 1/40 | |
| 9 | CD45 RA | FITC | 10 μL | 1/10 | 50000 |
| | Integrin β7 | PE | 10 μL | 1/10 | |
| | CD8 | PerCP | 5 μL | 1/20 | |
| | CCR9 | APC | 5 μL | 1/20 | |
| 10 | CD3 | FITC | 5 μL | 1/20 | 50000 |
| | Integrin β7 | PE | 10 μL | 1/10 | |
| | CD4 | PerCP | 5 μL | 1/20 | |
| | CCR9 | APC | 5 μL | 1/20 | |
| 11 | CD3 | FITC | 5 μL | 1/20 | 50000 |
| | Integrin β7 | PE | 10 μL | 1/10 | |
| | CD8 | PerCP | 5 μL | 1/20 | |
| | CCR9 | APC | 5 μL | 1/20 | |
| 12 | CD38 | FITC | 10 μL | 1/10 | 50000 |
| | Integrin β7 | PE | 10 μL | 1/10 | |
| | CD4 | PerCP | 5 μL | 1/20 | |
| | CD62L | APC | 2.5 μL | 1/40 | |

Human Regulatory T Cell Staining Kit

| Tube | Mixture Panel | Label | Mab prep in 100 μL | Dilution | Number of cells to acquire |
|---|---|---|---|---|---|
| 13 | Isotype control IgG2a | PE | 20 μL | 1/5 | 3000 |
| 14 | CD4/CD25 | FITC/APC | 20 μL mix | 1/20 & 1/5 | 50000 |
| | FoxP3 | PE | 20 μL | 1/5 | |

Blocking

PBMCs were divided into two tubes: tube A for blocking of PBMCs at about 2-4×10$^6$ lymphocytes/ml in RPMI; tube B for PBMCs for staining without blocking, diluted to about 1-2×10$^6$ lymphocytes/ml by addition of RPMI. PBMCs in tube A were blocked by incubating with normal human IgG (1/34 dilution) for 15 minutes at 2-8° C. protected from light.

Direct Staining (Tubes 1-12)

Antibody mixtures according to tubes 1-12 of the table above were prepared in FACS tubes (BD Falcon, VWR cat no 352052). Blocked PBMCs from tube A were added to tubes 9-11 and non-blocked PBMCs from tube B were added to tubes 1-8 and 12. FACS tubes 1-12 were vortexed gently and incubated for 30 minutes at 2-8° C. protected from light. Stained PBMCs were washed by adding 2 ml cold phosphate buffered saline (PBS, pH 7.4, Gibco cat no 10010-015, Fisher Scientific, Gothenburg, Sweden), vortexing gently, centrifuging (10 minutes, 400×g), and discarding the supernatant. Stained PBMCs were fixed by resuspension in 200 μl cold PBS-1% formaldehyde solution (3 parts PBS, pH 7.4, Gibco cat no 10010-015 to 1 part 4% formaldehyde solution, Apoteket cat no 34 24 36) and incubation at 2-8° C. overnight protected from light.

Staining with Human Regulatory T Cell Staining Kit (Tubes 13-14)

FACS tube 13 (see table above) was prepared with 100 μl non-blocked PBMCs from tube B. FACS tube 14 (see table above) was prepared for surface staining with 20 μl of the CD4 FITC/CD25 APC cocktail and 100 μl blocked PBMCs from tube A, vortexed gently, then incubated for 30 minutes at 2-8° C. protected from light. PBMCs in tubes 13 and 14 were washed by adding 2 ml cold PBS, vortexing gently, centrifuging (5 minutes, 400×g), and discarding the supernatant. PBMCs in tubes 13 and 14 were fixed by resuspension in 1 ml Fixation/Permeabilization Solution (one part Fixation/Permeabilization 4× Concentrate and three parts Fixation/Permeabilization Diluent) and incubation at 2-8° C. overnight protected from light.

Fixed PBMCs (tubes 13 and 14) were washed and permeabilized by centrifuging (10 minutes, 400×g) discarding the supernatant, resuspending in 2 ml 1× Permeabilization Buffer (one part 10× Permeabilization Buffer and nine parts distilled water), vortexing gently, repeating the preceding four steps again, and finally centrifuging again (10 minutes, 400×g). Permeabilized PBMCs in tube 14 were blocked with 2 µl normal rat serum by incubating for 15 minutes at 2-8° C. protected from light. Intracellular staining was performed by adding 20 µl rat IgG2a isotype control PE to tube 13 and 20 µl anti-human FoxP3 PE to tube 14, followed by incubation for 30 minutes at 2-8° C. protected from light. Stained PBMCs were washed with 2 ml PBS, gently vortexed, centrifuged (10 minutes, 400×g), and the supernatant was discarded before resuspending the cells in 200 µl PBS prior to flow cytometry analysis.

Flow Cytometry Analysis

The Becton Dickinson FACSCalibur® can detect 6 different parameters of a single particle or cell in an optical system. The instrument converts light scattering and fluorescence intensity into digital pulses. Forward Scatter (FSC) provides a measure of size and Side Scatter (SSC) provides a measure of cytoplasmic granularity. The instrument has four-color fluorescence detectors: the blue (488 nm) laser detects FL1, FL2 and FL3 and an additional red diode laser (635 nm) detects FL4.

After regular system cleaning of the instrument a calibration check with 3-color CaliBRITE Beads (BD no 340486) and CaliBRITE APC Beads (BD no 340487) and Auto-COMP™ Software was performed for setting photomultiplier tube (PMT) voltages and adjusting and optimizing the fluorescence compensation of the detectors (FL1; FL2, FL3 and FL4). The CaliBRITE beads are of exact size and are labelled with exact amount of fluorochromes simulating unstained and stained leucocytes. AutoCOMP™ Software generates a CalibFile. All of the monoclonal antibodies were pre-titrated with the Calib File instrument setting. CellQuest Pro Software was used to run the BD FACSCalibur. 3000-10000 acquired, collected and gated lymphocytes were measured for each tube according to the table above.

Isotype-matched control antibodies (IgG2/IgG1/CD4 isotype (FITC, PE and PerCP-Cy 5.5) and IgG1 isotype (APC), BD biosciences, CA USA) were used to set the dot plot quadrant and calculate the percent of lymphocyte populations through subtraction of contaminating non-lymphocytes. Lymphocytes were identified and gated in a dot plot displaying side scatter (cytoplasmic granularity) and FL1 parameter (FITC positive intensity) CD3+ T-cells. A multicolour back gate of lymphocytes was then shown in a FSC and SSC dot plot. A region was set around these identified lymphocytes (lymphocyte gate). New dot plots were displayed from the lymphocyte gate with different two-parameter combinations (FL1, FL2, FL3 and FL4) of the stained monoclonal antibodies of interest and the characteristic subsets were then identified. Quadrants were set in the two parameter dot plots from the isotype control, negative population. A subset is reported as a percentage of a quadrant population in the lymphocyte gate. Non-stained negative cells in lymphocyte gate were subtracted. The term "leucocytes" as used herein means PBMCs (i.e. the total population of isolated cells).

Specifically, subgroups of T cells, CD4+(Th) or CD8+ (Tc) cells were gated from the lymphocyte gate. From these gates, naïve cells were gated as CD3+CD4/CD8+CD45RA+CD45RO− and memory cells as CD3+CD4/CD8+CD45RA−CD45RO+. Activated and differentiated effector and memory cells were gated as CD3+CD$^4$/8+CD62L+, CD4+CD25+CD45RA+CD45RO+, CD4+CD25+CCR4+CD45RO, CD4+CD25+CCR4+CD62L+, CD8+CD45RA+CCR9+β7+, CD3+CD4+/CD8+β7+CCR9+, CD4+CD38+β7+CD62−. B cells were defined as CD3−CD19+ lymphocytes. From the lymphocyte gate, CD4+ cells were gated, followed by gating for CD25+ cells. This population was then examined for the expression of FoxP3+ cells. From the CD4+CD25+ gate, the percent with the highest CD25 expression, CD4+CD25$^{high}$ was determined. The CD4+CD25$^{high}$ lymphocyte population was then examined further for the expression of FoxP3. NK cells were gated from the lymphocyte gate. From this gate NK cells were gated as CD3−CD16+/CD56+ cells.

The lymphocyte assay region contained >70% lymphocytes. The intra-assay analysis of CD3+ T-cells showed a covariance of 3% and the inter-assay analysis of CD3+ T-cells showed a covariance of 5%.

Statistical Analysis

The study outcome was coeliac autoimmunity assessed as changes in serum levels of tTG autoantibodies (one child was excluded due to insufficient volumes) and changes in peripheral immune response of B cells, NK cells, and subpopulations of regulatory T cells after 6 months. Comparison between groups of binary variables was done by means of Fisher's exact test. Comparison between groups on continuous and ordered categorical data is done by the Wilcoxon Rank Sum test, e.g. Wilcoxon rank-sum test was used to compare tTGA levels between the probiotic-treated group with the placebo group at 0, 3 and 6 months. To compare the changes in tTGA levels over time within each group, Wilcoxon signed rank test for continuous variables was used. Levels of IgA-tTGA and IgG-tTGA were analyzed as separate data sets. Likewise, Wilcoxon rank-sum test was applied for the comparison between the probiotic-treated group and placebo, with regard to changes measured from baseline to 3 and 6 months for the parameters analysed by flow cytometry. Wilcoxon signed rank test was used for measuring the differences from baseline at 3 and 6 months within each group. A t-test was used to compare HLA distribution between groups.

Missing data were not imputed, i.e. the analyses are on observed cases. To avoid the effect of drop-outs and to restrict the comparison of the treatment to those children who adhered perfectly to the clinical trial instructions, intention-to-treat analysis and per-protocol-analysis were performed. All reported p-values are 2-sided and were not adjusted for multiplicity (i.e. nominal). A p-value of <0.05 was considered of statistical significance. Statistical analyses were performed in StatXact version 10.1 (Cytel, Cambridge, Mass., USA).

Results—Treatment with *L. paracasei* and *L. plantarum* Strains Reduces tTGA Autoantibodies in Celiac Disease Autoimmunity (CDA)

A total of 118 children fulfilled the inclusion criteria and were invited to study participation. Of those, 90 children and their caretakers agreed to study participation: 1 from the CiPiS study and the remaining 89 from the TEDDY study. Twelve (13%) of these left the study after the initial visit. One child was excluded due to blood samples being of insufficient volumes to perform tTGA analysis. In total, 77 (87%) children were included in the final data set; 40 (52%) in the probiotic-treated group and 37 (48%) in the placebo group, respectively. Baseline characteristics of these groups are shown in Table 3 and HLA distribution in Table 3A. Mean and median study duration was 188 and 190 days, respectively (Q1: 176.5 days, Q3: 203 days, spread 153-237 days).

TABLE 3

Baseline characteristics at start of study (first visit).

| | Treatment n = 40 | Placebo n = 37 | p-value |
|---|---|---|---|
| Age, years, mean | 4.85 | 4.42 | 0.284[1] |
| Sex, n | | | 0.172[2] |
| Boys | 22 | 14 | |
| Girls | 18 | 23 | |
| Weight, kg, mean | 22.0 | 20.8 | 0.182[1] |
| Length, cm, mean | 114.0 | 110.8 | 0.243[1] |

[1]Wilcoxon Rank Sum test, 2-sided;
[2]Fishers Exact test, 2-sided

TABLE 3A

HLA distribution of the study population.

| HLA-type | Probiotic group n (%) | Placebo group n (%) | p-value |
|---|---|---|---|
| DR3-DQ2/DR4-DQ8 | 10 (25.0) | 16 (42.1) | 0.112 |
| DR4-DQ8/DR4-DQ8 | 10 (25.0) | 7 (18.4) | 0.488 |
| DR4-DQ8/DR8/DQ4 | 4 (10.0) | 2 (5.2) | 0.439 |
| DR3-DQ2/DR3-DQ2 | 15 (37.5) | 13 (34.2) | 0.766 |
| DR4/DR1 | 1 (2.5) | 0 (0.0). | 0.333 |

TABLE 4

Tissue transglutaminase autoantibody (tTGA) levels, IgA and IgG. p-values are comparisons between treatment and placebo at each visit.

| | Visit 1 | Visit 2 (approx. 3 mo.) | Visit 3 (approx. 6. mo.) |
|---|---|---|---|
| tTGA-IgA, mean (median) | | | |
| Treatment | 158.60 (4.71) | 72.84 (3.07) | 55.41 (2.69) |
| Placebo | 12.96 (4.38) | 21.98 (4.93) | 38.23 (3.72) |
| p-value[1] | 0.8912 | 0.3013 | 0.6545 |
| tTGA-IgG, mean (median) | | | |
| Treatment | 166.98 (1.57) | 141.74 (1.64) | 86.35 (1.61) |
| Placebo | 8.00 (1.60) | 14.26 (1.56) | 64.33 (1.36) |
| p-value[1] | 0.8480 | 0.9373 | 0.5428 |

[1]Wilcoxon ranked sum test, 2-sided

After 3 months, levels of tTG-IgG decreased a mean 29.4±513 U/mL in the probiotic group and increased in the placebo group a mean 6.3±48 U/mL as compared to baseline levels (p=0.046 and p=0.034, respectively), but no significant difference in IgA-tTG levels between the groups was observed after 3 months. After 6 months, levels decreased for both IgA-tTG (mean decrease 107.0±855 U/mL; p=0.013) and IgG-tTG (mean decrease 84.7±748 U/mL; p=0.062) in the probiotic group, whereas the opposite was true for the placebo group, which showed increased levels for both IgA-tTG (mean increase 25.0±161 SD U/mL; p=0.043) and IgG-tTG (mean increase 56.2±349 U/mL; p=0.008) compared to baseline.

Results—Treatment with *L. paracasei* and *L. plantarum* Strains Decreases the Proportion of Natural Killer T Cells, Counteracts the Increased Proportion of Natural Killer Cells and Reduces CD62L Expression in Cytotoxic T Cells Flow cytometry analysis was used to examine any changes in the size and activation status of white blood cell populations at baseline and at each of the follow-up visits, in both study groups.

Table 5 shows that the percentage of natural killer T (NK-T) cells, identified as CD3+CD56+ cells, decreased with *Lactobacillus* treatment and the reduction was statistically significant by the second follow-up visit within the treatment group (p=0.0297) and between treatment and placebo groups (p=0.0079). Table 6 shows that the percentage of natural killer (NK) cells, identified as CD3−CD56+ increased statistically significant by the 6-months visit in the placebo group as compared to the probiotic group (p=0.0381).

Table 7 shows the number of cytotoxic T cells (CD3+CD8+), which were increased by a mean of 1.74% (p=0.017) in the placebo group at the first follow-up visit (3 months) only. Table 7A shows the proportion of gated $T_H$ cells (CD3+CD4+), which by the second follow-up visit (6 months) had decreased by a mean of 5.55% (p=0.039) in the placebo group, whereas no significant change was observed for the probiotic group.

Further to Table 7, the expression of CD62L on the surface of CD3+CD8+ cells in Tables 8 and 9 shows a statistical trend towards more $CD62L^{low}$ cytotoxic T cells (p=0.0815) and fewer $CD62L^{high}$ cytotoxic T cells (p=0.0729) with probiotic treatment compared to placebo at the second follow-up visit. CD62L is the cell adhesion molecule L-selectin, involved in lymphocyte interactions with endothelial cells, assisting entry into secondary lymphoid tissues. The presence of CD62L on the cell surface indicates a naïve state ($CD62L^{high}$) whereas when the cells have been activated they release CD62L from their surface ($CD62L^{low}$). Table 9A also shows fewer CD3+CD8+ $CD62L^{low}$ cells (mean 0.86% decrease, p=0.014) in the placebo group at the second follow-up visit, whereas no significant change was observed for the probiotic group.

Further to Table 7A, Table 9B shows a trend to a decrease in CD3+CD4+$CD62L^{low}$ cells in the placebo group (mean 5.55% decrease, p=0.039), whereas no significant change was observed for the probiotic group.

TABLE 5

NK-T cells CD3+CD56+ (% NK-T cells of lymphocytes)

| Group | Statistics | V0 | V1 | V2 | V1-V0 | V2-V0 |
|---|---|---|---|---|---|---|
| Lactobacilli | N | 33 | 39 | 38 | 32 | 31 |
| | Missing | 13 | 7 | 8 | 14 | 15 |
| | Min | 0.10 | 0.10 | 0.10 | −1.54 | −3.67 |
| | Median | 0.44 | 0.45 | 0.44 | −0.09 | −0.16 |
| | Max | 4.74 | 3.27 | 1.60 | 1.57 | 1.00 |
| | Mean | 0.77 | 0.67 | 0.51 | −0.12 | −0.29 |
| | Std | 0.85 | 0.62 | 0.34 | 0.66 | 0.81 |
| | P-value | NA | NA | NA | 0.2082 | 0.0297 |
| Placebo | N | 32 | 34 | 34 | 30 | 30 |
| | Missing | 12 | 10 | 10 | 14 | 14 |
| | Min | 0.12 | 0.22 | 0.19 | −0.95 | −0.94 |
| | Median | 0.46 | 0.49 | 0.58 | 0.02 | 0.18 |
| | Max | 1.26 | 1.30 | 2.35 | 0.97 | 1.72 |
| | Mean | 0.55 | 0.59 | 0.69 | 0.04 | 0.13 |
| | Std | 0.30 | 0.33 | 0.40 | 0.41 | 0.52 |
| | P-value | NA | NA | NA | 0.6815 | 0.1082 |
| P-value | | 0.4590 | 0.8238 | 0.0202 | 0.2316 | 0.0079 |

TABLE 6

| NK cells CD3−CD56+ (% NK cells of lymphocytes) | | | | | | |
|---|---|---|---|---|---|---|
| Group | Statistics | V0 | V1 | V2 | V1-V0 | V2-V0 |
| Lactobacilli | N | 33 | 39 | 38 | 32 | 31 |
| | Missing | 13 | 7 | 8 | 14 | 15 |
| | Min | 1.11 | 3.14 | 1.68 | −26.45 | −34.27 |
| | Median | 8.79 | 7.63 | 7.07 | 0.18 | −1.61 |
| | Max | 43.71 | 21.95 | 15.14 | 8.62 | 10.74 |
| | Mean | 10.69 | 8.33 | 7.76 | −2.01 | −2.86 |
| | Std | 8.99 | 4.55 | 3.50 | 7.54 | 9.81 |
| | P-value | NA | NA | NA | 0.4559 | 0.2639 |
| Placebo | N | 32 | 34 | 34 | 30 | 30 |
| | Missing | 12 | 10 | 10 | 14 | 14 |
| | Min | 2.37 | 1.99 | 3.08 | −11.55 | −6.78 |
| | Median | 7.18 | 7.11 | 7.65 | 1.80 | 2.18 |
| | Max | 26.01 | 27.77 | 47.42 | 9.55 | 21.41 |
| | Mean | 8.33 | 8.44 | 10.62 | 0.66 | 2.68 |
| | Std | 5.52 | 5.02 | 8.32 | 4.29 | 6.55 |
| | P-value | NA | NA | NA | 0.1347 | 0.0606 |
| P-value | | 0.2930 | 0.8842 | 0.2172 | 0.2194 | 0.0381 |

TABLE 7

| CD3+CD8+ (% cytotoxic T cells of CD3+ lymphocytes) | | | | | | |
|---|---|---|---|---|---|---|
| Group | Statistics | V0 | V1 | V2 | V1-V0 | V2-V0 |
| Lactobacilli | N | 32 | 39 | 38 | 31 | 30 |
| | Missing | 14 | 7 | 8 | 15 | 16 |
| | Min | 19.23 | 20.42 | 24.06 | −9.73 | −4.15 |
| | Median | 33.62 | 33.22 | 34.56 | 0.93 | 1.14 |
| | Max | 42.13 | 45.21 | 44.05 | 13.63 | 15.40 |
| | Mean | 32.51 | 33.50 | 34.08 | 1.24 | 2.10 |
| | Std | 6.22 | 6.04 | 5.67 | 4.47 | 4.94 |
| | P-value | NA | NA | NA | 0.1122 | 0.0732 |
| Placebo | N | 31 | 32 | 34 | 27 | 29 |
| | Missing | 13 | 12 | 10 | 17 | 15 |
| | Min | 17.62 | 17.33 | 17.47 | −4.17 | −14.04 |
| | Median | 32.39 | 33.08 | 31.86 | 1.12 | 0.31 |
| | Max | 47.94 | 50.53 | 47.49 | 9.93 | 16.86 |
| | Mean | 32.10 | 33.53 | 33.15 | 1.74 | 1.01 |
| | Std | 7.70 | 8.53 | 7.37 | 3.36 | 6.35 |
| | P-value | NA | NA | NA | 0.0171 | 0.6295 |
| P-value | | 0.6181 | 0.9679 | 0.4206 | 0.4643 | 0.4136 |

TABLE 7A

| CD3+ CD4+ (% T-helper cells of CD3+ leucocytes) | | | | | | |
|---|---|---|---|---|---|---|
| Group | Statistics | V0 | V1 | V2 | V1-V0 | V2-V0 |
| Lactobacilli | N | 32 | 39 | 38 | 31 | 30 |
| | Missing | 14 | 7 | 8 | 15 | 16 |
| | Min | 2.13 | 1.21 | 4.73 | −30.81 | −38.10 |
| | Median | 14.95 | 13.71 | 11.75 | −1.34 | −3.01 |
| | Max | 48.34 | 31.08 | 29.82 | 19.02 | 17.09 |
| | Mean | 17.04 | 13.84 | 14.63 | −2.47 | −3.44 |
| | Std | 9.78 | 7.36 | 6.79 | 12.40 | 12.63 |
| | P-value | NA | NA | NA | 0.3176 | 0.2286 |
| Placebo | N | 31 | 32 | 34 | 27 | 29 |
| | Missing | 13 | 12 | 10 | 17 | 15 |
| | Min | 1.06 | 6.40 | 0.93 | −32.01 | −31.93 |
| | Median | 14.04 | 13.30 | 13.35 | 0.04 | −4.07 |
| | Max | 50.33 | 35.42 | 29.26 | 11.53 | 14.57 |
| | Mean | 19.01 | 15.61 | 14.20 | −4.43 | −5.55 |
| | Std | 12.82 | 8.00 | 7.13 | 11.98 | 12.61 |
| | P-value | NA | NA | NA | 0.2508 | 0.0386 |
| P-value | | 0.8244 | 0.4243 | 0.8073 | 0.8649 | 0.6679 |

TABLE 8

CD3+CD8+CD62L$^{low}$ (% CD62L$^{low}$ of CD3+CD8+ cells or cytotoxic
T cells with low expression of CD62L as % of lymphocytes)

| Group | Statistics | V0 | V1 | V2 | V1-V0 | V2-V0 |
|---|---|---|---|---|---|---|
| Lactobacilli | N | 31 | 39 | 38 | 30 | 29 |
| | Missing | 15 | 7 | 8 | 16 | 17 |
| | Min | 12.93 | 11.02 | 12.99 | −30.81 | −22.56 |
| | Median | 30.01 | 25.78 | 28.38 | 0.12 | 2.86 |
| | Max | 61.80 | 70.98 | 90.33 | 43.51 | 60.32 |
| | Mean | 32.53 | 32.12 | 33.72 | 0.89 | 3.66 |
| | Std | 13.05 | 15.49 | 18.31 | 17.39 | 16.52 |
| | P-value | NA | NA | NA | 1.0000 | 0.3495 |
| Placebo | N | 31 | 32 | 34 | 27 | 29 |
| | Missing | 13 | 12 | 10 | 17 | 15 |
| | Min | 8.59 | 10.38 | 13.17 | −25.80 | −21.86 |
| | Median | 33.01 | 28.55 | 25.92 | −2.69 | −3.39 |
| | Max | 55.58 | 63.70 | 68.32 | 55.02 | 34.12 |
| | Mean | 32.15 | 31.07 | 28.73 | −0.63 | −3.25 |
| | Std | 10.91 | 14.24 | 13.44 | 15.51 | 14.66 |
| | P-value | NA | NA | NA | 0.5619 | 0.1622 |
| P-value | | 1.0000 | 0.7983 | 0.3736 | 0.7692 | 0.0815 |

TABLE 9

CD3+CD8+ CD62L$^{high}$ (% CD62L$^{high}$ of CD3+CD8+ cells
or % cytotoxic T cells with high expression of CD62L)

| Group | Statistics | V0 | V1 | V2 | V1-V0 | V2-V0 |
|---|---|---|---|---|---|---|
| Lactobacilli | N | 31 | 39 | 38 | 30 | 29 |
| | Missing | 15 | 7 | 8 | 16 | 17 |
| | Min | 38.20 | 28.91 | 7.83 | −43.45 | −61.92 |
| | Median | 69.75 | 73.68 | 71.19 | −0.19 | −2.72 |
| | Max | 87.07 | 88.73 | 86.80 | 31.37 | 22.56 |
| | Mean | 67.25 | 67.68 | 65.74 | −0.87 | −4.07 |
| | Std | 13.13 | 15.42 | 18.30 | 17.46 | 16.37 |
| | P-value | NA | NA | NA | 1.0000 | 0.2867 |
| Placebo | N | 31 | 32 | 34 | 27 | 29 |
| | Missing | 13 | 12 | 10 | 17 | 15 |
| | Min | 44.42 | 35.40 | 31.27 | −56.01 | −34.20 |
| | Median | 66.93 | 71.24 | 73.51 | 3.18 | 3.26 |
| | Max | 91.41 | 89.62 | 86.56 | 25.80 | 21.86 |
| | Mean | 67.62 | 68.63 | 71.03 | 0.56 | 3.24 |
| | Std | 10.91 | 14.31 | 13.40 | 15.51 | 14.65 |
| | P-value | NA | NA | NA | 0.4846 | 0.1689 |
| P-value | | 0.9554 | 0.8206 | 0.3001 | 0.7212 | 0.0729 |

TABLE 9A

CD3+CD8+ CD62L$^{low}$ (% CD62L$^{low}$ of CD3+CD8+ cells or cytotoxic
T cells with low expression of CD62L as % of leucocytes)

| Group | Statistics | V0 | V1 | V2 | V1-V0 | V2-V0 |
|---|---|---|---|---|---|---|
| Lactobacilli | N | 31 | 39 | 38 | 30 | 29 |
| | Missing | 15 | 7 | 8 | 16 | 17 |
| | Min | 0.62 | 0.14 | 0.57 | −3.63 | −5.08 |
| | Median | 2.53 | 2.11 | 2.43 | −0.37 | −0.10 |
| | Max | 10.30 | 14.95 | 7.67 | 12.94 | 4.87 |
| | Mean | 2.91 | 2.54 | 2.75 | 0.01 | −0.01 |
| | Std | 2.05 | 2.37 | 1.61 | 2.84 | 1.93 |
| | P-value | NA | NA | NA | 0.2917 | 0.7922 |
| Placebo | N | 31 | 32 | 34 | 27 | 29 |
| | Missing | 13 | 12 | 10 | 17 | 15 |
| | Min | 0.20 | 0.63 | 0.23 | −5.70 | −4.99 |
| | Median | 2.70 | 2.26 | 2.02 | −0.31 | −0.85 |
| | Max | 8.68 | 7.48 | 7.66 | 4.58 | 4.78 |

TABLE 9A-continued

CD3+CD8+ CD62L$^{low}$ (% CD62L$^{low}$ of CD3+CD8+ cells or cytotoxic
T cells with low expression of CD62L as % of leucocytes)

| Group | Statistics | V0 | V1 | V2 | V1-V0 | V2-V0 |
|---|---|---|---|---|---|---|
|  | Mean | 2.98 | 2.62 | 2.24 | −0.45 | −0.86 |
|  | Std | 2.03 | 1.58 | 1.56 | 1.89 | 2.09 |
|  | P-value | NA | NA | NA | 0.2087 | 0.0143 |
| P-value |  | 0.7241 | 0.5793 | 0.1456 | 0.8460 | 0.0879 |

TABLE 9B

CD3+CD4+ CD62L$^{low}$ (% CD62L$^{low}$ of CD3+CD4+ cells or T-helper
cells with low expression of CD62L as % of leucocytes)

| Group | Statistics | V0 | V1 | V2 | V1-V0 | V2-V0 |
|---|---|---|---|---|---|---|
| Lactobacilli | N | 31 | 39 | 38 | 30 | 29 |
|  | Missing | 15 | 7 | 8 | 16 | 17 |
|  | Min | 0.35 | 0.31 | 0.63 | −5.97 | −5.16 |
|  | Median | 2.42 | 1.74 | 1.85 | −0.47 | −0.67 |
|  | Max | 7.69 | 17.53 | 10.62 | 15.99 | 5.43 |
|  | Mean | 2.83 | 2.45 | 2.59 | −0.30 | −0.18 |
|  | Std | 1.80 | 2.92 | 2.05 | 3.64 | 2.44 |
|  | P-value | NA | NA | NA | 0.1446 | 0.3330 |
| Placebo | N | 31 | 32 | 34 | 27 | 29 |
|  | Missing | 13 | 12 | 10 | 17 | 15 |
|  | Min | 0.27 | 0.61 | 0.13 | −4.93 | −6.83 |
|  | Median | 2.56 | 2.19 | 2.06 | −0.23 | −0.83 |
|  | Max | 10.62 | 5.69 | 6.82 | 3.67 | 2.86 |
|  | Mean | 3.25 | 2.41 | 2.31 | −0.86 | −0.91 |
|  | Std | 2.20 | 1.38 | 1.54 | 1.98 | 2.15 |
|  | P-value | NA | NA | NA | 0.0702 | 0.0506 |
| P-value |  | 0.4414 | 0.2857 | 0.6680 | 0.8336 | 0.4559 |

Results—Treatment with *L. paracasei* and *L. plantarum* Strains Prevents an Increase in Activation of T Helper Cells (CD4+CD25+ Cells) and an Increase in CD4+CD25+ FoxP3+ Cells Further flow cytometry analysis focused on T helper cells, identified as CD3+CD4+, with sub-populations of CD4+ T helper cells differing between the two study groups.

Table 10 shows that the population of naïve $T_H$ cells (CD4+CD45RA+CD45RO−) at the second follow-up visit (6 months) had decreased by a mean of 4.73% (p=0.002) in the placebo group. Table 10 also shows that *Lactobacillus* treatment prevented this decrease in the proportion of cells with the naïve T cell marker CD45RA+/RO− compared to placebo (p=0.0532 for V1-V0; p=0.0217 for V2-V0). Conversely, Table 11 shows that the population of memory $T_H$ cells (CD4+CD45RA−CD45RO+) increased by a mean of 3.07% (p=0.003) in the placebo group by the second follow-up visit (6 months). Table 11 also shows that *Lactobacillus* treatment prevented this increase in the proportion of cells with the memory T cell marker CD45RA−/RO+ compared to placebo (p=0.0650 for V1-V0; p=0.0198 for V2-V0).

Table 10A shows that the population of naïve $T_C$ cells (CD8+CD45RA+CD45RO−) at the second follow-up visit (6 months) had decreased by a mean of 2.17% (p=0.030) in the placebo group, whereas no significant change was observed for the probiotic group.

*Lactobacillus* treatment also prevented an increase in the percentage of memory (CD45RO+) T-helper cells, compared to placebo (Tables 12-15), and prevented an increase in the percentage of memory $T_H$ cells expressing CCR4 (CD4+CD45RO+CCR4+) (placebo group mean increase 7.63%, p=0.003; comparative p=0.0110; Table 15A).

*Lactobacillus* treatment prevents a decrease in CD4+CD38+CD62L− T helper cells, expressing the CD38 ectoenzyme and glycoprotein cell adhesion molecule but not L-selectin (CD62L), with a trend at the second follow-up visit (Table 16, p=0.0753). Treatment also prevents a decrease in CD4+CCR9+β7+ T helper cells observed at the second follow-up visit (Table 17, p=0.0382). The expression of β7 (from the gut homing receptor α4β7) on the surface of T cells is regarded as characteristic of intestinal homing cells.

Table 18 shows that *Lactobacillus* treatment prevented an increase in the proportion of activated T helper cells by the second follow-up visit, where activation is identified by CD25, namely the interleukin-2 receptor alpha chain. Table 18A shows that the percentage of naïve CD4+CD25+CD45RA+ cells decreased by a mean of 5.72% (p=0.0179) in the placebo group by the second follow-up visit (6 months), whereas no significant change was observed for the probiotic group.

Table 19 further shows that *Lactobacillus* treatment by the second follow-up visit, prevented an increase in the proportion of Tregulatory cells, identified as CD4+ cells with high CD25 positivity (CD25$^{high}$).

Table 20 shows a trend to an increase in the percentage of CD4+CD25+FoxP3+ cells in the placebo group by the second follow-up visit (mean increase of 0.32%, p=0.0521), and a significant effect overall of the probiotic treatment compared to placebo (p=0.0275).

TABLE 10

CD4+CD45RA+RO− (% CD45RA+CD45RO− of CD3+CD4+ cells
or naïve T-helper cells as % of lymphocytes)

| Group | Statistics | V0 | V1 | V2 | V1-V0 | V2-V0 |
|---|---|---|---|---|---|---|
| Lactobacilli | N | 32 | 39 | 38 | 31 | 30 |
|  | Missing | 14 | 7 | 8 | 15 | 16 |
|  | Min | 38.93 | 48.45 | 49.57 | −16.37 | −14.55 |
|  | Median | 68.60 | 66.79 | 65.01 | 1.78 | −0.59 |
|  | Max | 80.51 | 83.83 | 78.37 | 26.60 | 17.89 |
|  | Mean | 65.25 | 66.88 | 65.68 | 1.75 | −0.08 |
|  | Std | 9.63 | 8.00 | 7.95 | 8.17 | 6.92 |
|  | P-value | NA | NA | NA | 0.3105 | 0.7457 |

TABLE 10-continued

CD4+CD45RA+RO− (% CD45RA+CD45RO− of CD3+CD4+ cells or naive T-helper cells as % of lymphocytes)

| Group | Statistics | V0 | V1 | V2 | V1-V0 | V2-V0 |
|---|---|---|---|---|---|---|
| Placebo | N | 31 | 32 | 34 | 27 | 29 |
| | Missing | 13 | 12 | 10 | 17 | 15 |
| | Min | 42.72 | 46.64 | 47.24 | −19.50 | −28.78 |
| | Median | 71.52 | 68.41 | 68.87 | −1.72 | −4.03 |
| | Max | 85.28 | 82.13 | 82.39 | 12.27 | 19.53 |
| | Mean | 69.70 | 67.91 | 65.87 | −2.79 | −4.73 |
| | Std | 9.62 | 9.12 | 9.00 | 7.67 | 8.80 |
| | P-value | NA | NA | NA | 0.0692 | 0.0017 |
| P-value | | 0.0420 | 0.4672 | 0.7901 | 0.0532 | 0.0217 |

TABLE 10A

CD8+ CD45RA+RO− (% CD45RA+CD45RO− of CD3+CD8+ cells or naive cytotoxic T cells as % of leucocytes)

| Group | Statistics | V0 | V1 | V2 | V1-V0 | V2-V0 |
|---|---|---|---|---|---|---|
| Lactobacilli | N | 32 | 39 | 38 | 31 | 30 |
| | Missing | 14 | 7 | 8 | 15 | 16 |
| | Min | 0.85 | 0.52 | 1.96 | −9.82 | −9.82 |
| | Median | 5.23 | 5.39 | 5.79 | −0.12 | −0.26 |
| | Max | 14.25 | 17.78 | 15.00 | 10.20 | 7.09 |
| | Mean | 6.29 | 6.06 | 6.16 | 0.10 | −0.58 |
| | Std | 3.61 | 3.62 | 3.07 | 5.13 | 4.34 |
| | P-value | NA | NA | NA | 0.9655 | 0.4016 |
| Placebo | N | 31 | 32 | 34 | 27 | 29 |
| | Missing | 13 | 12 | 10 | 17 | 15 |
| | Min | 0.94 | 2.03 | 0.59 | −20.68 | −20.47 |
| | Median | 5.57 | 4.67 | 4.70 | −1.24 | −1.71 |
| | Max | 23.89 | 15.68 | 14.23 | 6.07 | 9.28 |
| | Mean | 7.27 | 5.94 | 5.44 | −1.88 | −2.17 |
| | Std | 5.07 | 3.64 | 3.35 | 4.99 | 5.38 |
| | P-value | NA | NA | NA | 0.0731 | 0.0308 |
| P-value | | 0.6745 | 0.7197 | 0.2647 | 0.2156 | 0.1951 |

TABLE 11

CD4+CD45RA−RO+ (% CD45RA−CD45RO+ of CD3+CD4+ cells or % memory T-helper cells)

| Group | Statistics | V0 | V1 | V2 | V1-V0 | V2-V0 |
|---|---|---|---|---|---|---|
| Lactobacilli | N | 32 | 39 | 38 | 31 | 30 |
| | Missing | 14 | 7 | 8 | 15 | 16 |
| | Min | 5.36 | 1.96 | 9.45 | −15.41 | −10.50 |
| | Median | 18.46 | 17.46 | 18.40 | −0.25 | 0.05 |
| | Max | 43.39 | 27.98 | 35.53 | 5.00 | 9.07 |
| | Mean | 19.61 | 17.00 | 18.72 | −1.95 | −0.34 |
| | Std | 8.58 | 5.71 | 6.20 | 6.05 | 5.42 |
| | P-value | NA | NA | NA | 0.2336 | 0.8513 |
| Placebo | N | 31 | 32 | 34 | 27 | 29 |
| | Missing | 13 | 12 | 10 | 17 | 15 |
| | Min | 0.84 | 0.28 | 0.31 | −6.51 | −5.91 |
| | Median | 14.89 | 14.47 | 17.85 | 0.23 | 3.82 |
| | Max | 30.44 | 40.92 | 30.94 | 17.82 | 11.81 |
| | Mean | 15.69 | 16.37 | 17.76 | 1.53 | 3.07 |
| | Std | 6.03 | 7.51 | 7.24 | 5.21 | 4.82 |
| | P-value | NA | NA | NA | 0.2220 | 0.0032 |
| P-value | | 0.0749 | 0.4463 | 0.6040 | 0.0650 | 0.0198 |

TABLE 12

CD4+CD25+CD45RO+ (% CD45RO+ of CD3+CD4+CD25+ cells
or % memory cells of T-helper cells expressing CD25)

| Group | Statistics | V0 | V1 | V2 | V1-V0 | V2-V0 |
|---|---|---|---|---|---|---|
| Lactobacilli | N | 32 | 39 | 38 | 31 | 30 |
| | Missing | 14 | 7 | 8 | 15 | 16 |
| | Min | 4.30 | 20.03 | 29.09 | −54.63 | −34.75 |
| | Median | 49.80 | 48.33 | 49.82 | 0.54 | 4.67 |
| | Max | 79.94 | 81.02 | 75.62 | 38.33 | 22.71 |
| | Mean | 50.68 | 49.47 | 50.48 | 0.51 | 0.94 |
| | Std | 17.76 | 14.48 | 11.69 | 15.44 | 12.57 |
| | P-value | NA | NA | NA | 0.5814 | 0.4161 |
| Placebo | N | 32 | 33 | 33 | 29 | 29 |
| | Missing | 12 | 11 | 11 | 15 | 15 |
| | Min | 1.36 | 4.51 | 21.47 | −25.54 | −26.73 |
| | Median | 44.76 | 42.96 | 48.32 | 2.13 | 12.56 |
| | Max | 66.91 | 76.11 | 79.29 | 45.63 | 60.72 |
| | Mean | 41.87 | 44.75 | 52.11 | 3.18 | 11.75 |
| | Std | 15.19 | 15.84 | 15.63 | 14.01 | 17.00 |
| | P-value | NA | NA | NA | 0.2770 | 0.0006 |
| | P-value | 0.0536 | 0.2195 | 0.7440 | 0.7690 | 0.0027 |

TABLE 13

CD4+CD25+CCR4+ CD45RO+ (% CD45RO+ of CD4+CD25+CCR4+
cells) (% memory cells of the T-helper cells expressing both CD25 and CCR4)

| Group | Statistics | V0 | V1 | V2 | V1-V0 | V2-V0 |
|---|---|---|---|---|---|---|
| Lactobacilli | N | 32 | 39 | 38 | 31 | 30 |
| | Missing | 14 | 7 | 8 | 15 | 16 |
| | Min | 0.00 | 50.16 | 48.73 | −16.72 | −30.75 |
| | Median | 70.63 | 74.93 | 72.53 | 3.15 | 2.40 |
| | Max | 91.41 | 91.89 | 92.78 | 64.64 | 20.14 |
| | Mean | 69.16 | 73.65 | 72.40 | 4.13 | 1.96 |
| | Std | 16.42 | 9.60 | 11.23 | 14.97 | 11.94 |
| | P-value | NA | NA | NA | 0.1406 | 0.2367 |
| Placebo | N | 32 | 33 | 33 | 29 | 29 |
| | Missing | 12 | 11 | 11 | 15 | 15 |
| | Min | 7.09 | 47.80 | 42.75 | −23.37 | −10.71 |
| | Median | 68.36 | 72.43 | 75.77 | 2.30 | 6.65 |
| | Max | 91.72 | 87.69 | 97.06 | 53.46 | 57.05 |
| | Mean | 67.18 | 71.72 | 75.98 | 4.06 | 9.38 |
| | Std | 15.39 | 9.70 | 11.15 | 12.95 | 13.82 |
| | P-value | NA | NA | NA | 0.0760 | 0.0007 |
| | P-value | 0.4407 | 0.4513 | 0.1512 | 0.9181 | 0.0825 |

TABLE 14

CD4+CD25$^{high}$ CD45RO+ (% CD45RO+ of CD4+CD25$^{high}$ cells or % memory
cells of the T-helper cells with high expression of CD25)

| Group | Statistics | V0 | V1 | V2 | V1-V0 | V2-V0 |
|---|---|---|---|---|---|---|
| Lactobacilli | N | 32 | 39 | 38 | 31 | 30 |
| | Missing | 14 | 7 | 8 | 15 | 16 |
| | Min | 3.80 | 21.34 | 25.97 | −53.86 | −39.60 |
| | Median | 45.89 | 48.07 | 46.22 | −0.95 | −0.41 |
| | Max | 82.58 | 84.63 | 71.63 | 39.87 | 30.38 |
| | Mean | 48.43 | 46.67 | 47.65 | −0.12 | −0.29 |
| | Std | 18.10 | 15.41 | 12.85 | 15.80 | 15.81 |
| | P-value | NA | NA | NA | 0.7905 | 0.8872 |
| Placebo | N | 32 | 32 | 33 | 28 | 29 |
| | Missing | 12 | 12 | 11 | 16 | 15 |
| | Min | 1.82 | 14.37 | 19.27 | −35.46 | −41.68 |
| | Median | 41.13 | 40.76 | 44.30 | 0.45 | 7.78 |
| | Max | 73.40 | 77.40 | 93.43 | 44.43 | 63.66 |

TABLE 14-continued

CD4+CD25$^{high}$ CD45RO+ (% CD45RO+ of CD4+CD25$^{high}$ cells or % memory cells of the T-helper cells with high expression of CD25)

| Group | Statistics | V0 | V1 | V2 | V1-V0 | V2-V0 |
|---|---|---|---|---|---|---|
| | Mean | 41.22 | 42.91 | 49.31 | 1.53 | 9.35 |
| | Std | 17.19 | 16.16 | 18.32 | 16.54 | 21.65 |
| | P-value | NA | NA | NA | 0.6456 | 0.0121 |
| P-value | | 0.1316 | 0.2188 | 0.9315 | 0.7891 | 0.0456 |

TABLE 15

CD4+CD25$^{high}$ CCR4+ CD45RO+ (% CD45RO+ of CD4+CD25$^{high}$CCR4+ cells or % memory T-helper cells expressing CCR4 and high levels of CD25)

| Group | Statistics | V0 | V1 | V2 | V1-V0 | V2-V0 |
|---|---|---|---|---|---|---|
| Lactobacilli | N | 32 | 39 | 38 | 31 | 30 |
| | Missing | 14 | 7 | 8 | 15 | 16 |
| | Min | 0.00 | 52.12 | 55.22 | −19.05 | −20.84 |
| | Median | 75.68 | 79.65 | 78.81 | 0.47 | 3.97 |
| | Max | 97.30 | 92.41 | 95.63 | 70.53 | 28.18 |
| | Mean | 73.10 | 77.16 | 77.04 | 3.32 | 1.84 |
| | Std | 17.86 | 9.84 | 10.22 | 16.78 | 11.65 |
| | P-value | NA | NA | NA | 0.5136 | 0.3259 |
| Placebo | N | 32 | 32 | 33 | 28 | 29 |
| | Missing | 12 | 12 | 11 | 16 | 15 |
| | Min | 9.93 | 45.90 | 34.09 | −21.33 | −22.60 |
| | Median | 73.76 | 77.93 | 82.87 | 3.82 | 7.88 |
| | Max | 94.87 | 89.46 | 98.37 | 64.49 | 66.47 |
| | Mean | 71.24 | 75.47 | 81.30 | 4.20 | 10.67 |
| | Std | 17.52 | 10.28 | 12.33 | 16.12 | 17.87 |
| | P-value | NA | NA | NA | 0.2183 | 0.0011 |
| P-value | | 0.6383 | 0.5311 | 0.0492 | 0.9790 | 0.0452 |

TABLE 15A

CD4+ CCR4+ CD45RO+ (% memory T-helper cells expressing CDR4 on their surface)

| Group | Statistics | V0 | V1 | V2 | V1-V0 | V2-V0 |
|---|---|---|---|---|---|---|
| Lactobacilli | N | 32 | 39 | 38 | 31 | 30 |
| | Missing | 14 | 7 | 8 | 15 | 16 |
| | Min | 1.71 | 44.95 | 38.12 | −33.51 | −27.79 |
| | Median | 65.03 | 70.17 | 66.43 | 1.27 | 0.50 |
| | Max | 90.03 | 90.63 | 86.20 | 64.29 | 17.88 |
| | Mean | 64.95 | 68.80 | 66.81 | 2.74 | −0.32 |
| | Std | 15.29 | 9.60 | 10.60 | 15.27 | 10.20 |
| | P-value | NA | NA | NA | 0.1461 | 1.0000 |
| Placebo | N | 32 | 33 | 34 | 29 | 30 |
| | Missing | 12 | 11 | 10 | 15 | 14 |
| | Min | 6.23 | 39.83 | 40.82 | −19.87 | −23.38 |
| | Median | 65.73 | 68.45 | 69.99 | 3.22 | 5.86 |
| | Max | 84.23 | 90.04 | 90.64 | 33.60 | 41.56 |
| | Mean | 62.97 | 67.78 | 70.12 | 4.63 | 7.63 |
| | Std | 15.11 | 10.42 | 11.82 | 12.77 | 13.92 |
| | P-value | NA | NA | NA | 0.0920 | 0.0026 |
| P-value | | 0.7338 | 0.7553 | 0.1900 | 0.5179 | 0.0110 |

TABLE 16

CD4+CD62L$^{low}$ CD38+ (% CD62L$^{low}$ of CD38+ CD4+ or % of T-helper cells expressing CD38 and low levels of CD62L)

| Group | Statistics | V0 | V1 | V2 | V1-V0 | V2-V0 |
|---|---|---|---|---|---|---|
| Lactobacilli | N | 30 | 39 | 38 | 29 | 28 |
| | Missing | 16 | 7 | 8 | 17 | 18 |
| | Min | 1.30 | 1.42 | 0.94 | −8.68 | −6.11 |
| | Median | 3.90 | 3.86 | 3.57 | −0.15 | 0.64 |
| | Max | 10.53 | 20.90 | 23.76 | 7.98 | 19.44 |
| | Mean | 4.89 | 5.32 | 5.58 | 0.17 | 1.03 |
| | Std | 3.03 | 4.01 | 4.45 | 3.87 | 5.00 |
| | P-value | NA | NA | NA | 0.6740 | 0.5670 |
| Placebo | N | 31 | 32 | 33 | 27 | 28 |
| | Missing | 13 | 12 | 11 | 17 | 16 |
| | Min | 1.08 | 1.03 | 1.33 | −10.31 | −12.08 |
| | Median | 5.23 | 3.41 | 3.97 | −1.11 | −1.32 |
| | Max | 15.50 | 20.62 | 20.32 | 14.44 | 17.54 |
| | Mean | 6.52 | 5.50 | 5.31 | −0.89 | −1.29 |
| | Std | 4.12 | 4.88 | 3.90 | 5.04 | 5.50 |
| | P-value | NA | NA | NA | 0.1111 | 0.0735 |
| P-value | | 0.1292 | 0.4923 | 0.9202 | 0.1856 | 0.0753 |

TABLE 17

CD4+CCR9+ β7+ (% of CD4+ cells positive for CCR9 and integrin β7)

| Group | Statistics | V0 | V1 | V2 | V1-V0 | V2-V0 |
|---|---|---|---|---|---|---|
| Lactobacilli | N | 32 | 39 | 38 | 31 | 30 |
| | Missing | 14 | 7 | 8 | 15 | 16 |
| | Min | 0.72 | 0.41 | 0.52 | −4.42 | −2.67 |
| | Median | 1.34 | 1.26 | 1.46 | −0.13 | 0.21 |
| | Max | 5.96 | 5.62 | 5.40 | 1.40 | 4.32 |
| | Mean | 1.68 | 1.44 | 1.71 | −0.41 | 0.06 |
| | Std | 1.11 | 0.88 | 0.94 | 1.12 | 1.25 |
| | P-value | NA | NA | NA | 0.0703 | 0.6227 |
| Placebo | N | 32 | 31 | 34 | 27 | 30 |
| | Missing | 12 | 13 | 10 | 17 | 14 |
| | Min | 0.60 | 0.59 | 0.37 | −7.10 | −5.40 |
| | Median | 1.65 | 1.61 | 1.42 | −0.03 | −0.33 |
| | Max | 8.71 | 2.68 | 3.31 | 1.24 | 1.79 |
| | Mean | 2.07 | 1.62 | 1.61 | −0.46 | −0.57 |
| | Std | 1.62 | 0.63 | 0.74 | 1.75 | 1.36 |
| | P-value | NA | NA | NA | 0.5342 | 0.0237 |
| P-value | | 0.2378 | 0.0848 | 0.7900 | 0.4932 | 0.0382 |

TABLE 18

CD4+CD25+ (% CD25+ of CD3+CD4+ cells or % of T-helper cells positive for CD25)

| Group | Statistics | V0 | V1 | V2 | V1-V0 | V2-V0 |
|---|---|---|---|---|---|---|
| Lactobacilli | N | 32 | 39 | 38 | 31 | 30 |
| | Missing | 14 | 7 | 8 | 15 | 16 |
| | Min | 4.78 | 5.25 | 5.54 | −8.36 | −6.83 |
| | Median | 8.82 | 9.85 | 8.83 | 0.13 | −0.10 |
| | Max | 19.55 | 15.51 | 19.82 | 7.03 | 8.12 |
| | Mean | 9.80 | 9.84 | 9.57 | 0.16 | −0.12 |
| | Std | 3.65 | 2.21 | 2.99 | 3.44 | 4.21 |
| | P-value | NA | NA | NA | 0.7151 | 0.8078 |
| Placebo | N | 32 | 33 | 33 | 29 | 29 |
| | Missing | 12 | 11 | 11 | 15 | 15 |
| | Min | 3.03 | 4.53 | 4.70 | −5.89 | −6.79 |
| | Median | 9.15 | 9.89 | 9.88 | 1.15 | 1.37 |
| | Max | 20.66 | 15.39 | 18.29 | 5.76 | 12.74 |
| | Mean | 9.76 | 10.02 | 10.60 | 0.66 | 1.60 |
| | Std | 3.76 | 2.69 | 3.83 | 3.06 | 3.74 |
| | P-value | NA | NA | NA | 0.1828 | 0.0121 |
| P-value | | 0.9628 | 0.9217 | 0.3423 | 0.4124 | 0.0971 |

TABLE 18A

CD4+ CD25+ total CD45RA+ (% naïve CD4+ cells expressing CD25 on their surface)

| Group | Statistics | V0 | V1 | V2 | V1-V0 | V2-V0 |
|---|---|---|---|---|---|---|
| Lactobacilli | N | 31 | 39 | 38 | 30 | 29 |
| | Missing | 15 | 7 | 8 | 16 | 17 |
| | Min | 3.05 | 11.46 | 10.09 | −23.80 | −21.93 |
| | Median | 28.76 | 35.65 | 30.19 | 0.78 | −0.80 |
| | Max | 57.29 | 56.58 | 59.50 | 32.86 | 18.99 |
| | Mean | 31.03 | 33.89 | 31.67 | 1.48 | −1.18 |
| | Std | 14.08 | 11.63 | 11.48 | 11.96 | 9.86 |
| | P-value | NA | NA | NA | 0.6554 | 0.5221 |
| Placebo | N | 32 | 33 | 33 | 29 | 29 |
| | Missing | 12 | 11 | 11 | 15 | 15 |
| | Min | 19.96 | 15.04 | 12.36 | −33.69 | −32.45 |
| | Median | 39.71 | 35.61 | 35.89 | −3.86 | −3.76 |
| | Max | 72.86 | 65.34 | 73.61 | 19.31 | 10.99 |
| | Mean | 38.69 | 37.03 | 33.75 | −3.38 | −5.72 |
| | Std | 12.72 | 14.35 | 13.59 | 11.28 | 11.09 |
| | P-value | NA | NA | NA | 0.1373 | 0.0179 |
| P-value | | 0.0316 | 0.4770 | 0.6121 | 0.1244 | 0.1930 |

TABLE 19

CD4+CD25$^{high}$ (% of CD4+ cells highly positive for CD25, regarded as T regulatory cells).

| Group | Statistics | V0 | V1 | V2 | V1-V0 | V2-V0 |
|---|---|---|---|---|---|---|
| Lactobacilli | N | 32 | 39 | 38 | 31 | 30 |
| | Missing | 14 | 7 | 8 | 15 | 16 |
| | Min | 1.83 | 2.12 | 2.22 | −4.60 | −4.14 |
| | Median | 3.93 | 4.52 | 4.30 | 0.52 | 0.08 |
| | Max | 9.31 | 7.11 | 8.58 | 3.91 | 3.23 |
| | Mean | 4.17 | 4.36 | 4.22 | 0.29 | 0.04 |
| | Std | 1.62 | 1.10 | 1.33 | 1.66 | 1.98 |
| | P-value | NA | NA | NA | 0.2260 | 0.8670 |
| Placebo | N | 32 | 33 | 33 | 29 | 29 |
| | Missing | 12 | 11 | 11 | 15 | 15 |
| | Min | 1.25 | 2.03 | 1.56 | −3.54 | −3.35 |
| | Median | 4.04 | 4.38 | 4.63 | 0.38 | 1.06 |
| | Max | 8.99 | 7.52 | 8.26 | 3.64 | 5.39 |
| | Mean | 4.21 | 4.49 | 4.76 | 0.47 | 0.90 |
| | Std | 1.63 | 1.37 | 1.71 | 1.54 | 1.82 |
| | P-value | NA | NA | NA | 0.0846 | 0.0081 |
| P-value | | 0.8493 | 0.8332 | 0.1720 | 0.7831 | 0.1026 |

TABLE 20

CD4+CD25+Foxp3+ (T-regulatory cells as % of leucocytes)

| Group | Statistics | V0 | V1 | V2 | V1-V0 | V2-V0 |
|---|---|---|---|---|---|---|
| Lactobacilli | N | 31 | 39 | 38 | 30 | 29 |
| | Missing | 15 | 7 | 8 | 16 | 17 |
| | Min | 0.22 | 0.18 | 0.17 | −1.78 | −2.11 |
| | Median | 1.62 | 1.74 | 1.50 | 0.04 | −0.15 |
| | Max | 3.58 | 2.88 | 3.22 | 2.10 | 1.30 |
| | Mean | 1.55 | 1.67 | 1.45 | 0.11 | −0.20 |
| | Std | 0.79 | 0.66 | 0.64 | 0.86 | 0.87 |
| | P-value | NA | NA | NA | 0.4995 | 0.3276 |
| Placebo | N | 29 | 33 | 34 | 26 | 27 |
| | Missing | 15 | 11 | 10 | 18 | 17 |
| | Min | 0.29 | 0.83 | 0.08 | −0.84 | −1.71 |
| | Median | 1.57 | 1.78 | 1.83 | 0.14 | 0.31 |
| | Max | 2.75 | 3.43 | 3.78 | 1.32 | 2.32 |
| | Mean | 1.54 | 1.74 | 1.82 | 0.19 | 0.32 |
| | Std | 0.64 | 0.54 | 0.85 | 0.64 | 0.91 |
| | P-value | NA | NA | NA | 0.1711 | 0.0521 |
| P-value | | 0.8515 | 0.9351 | 0.0326 | 0.6866 | 0.0275 |

DISCUSSION

The major finding of importance in this study was the retardation of increase in tTG autoantibody levels by use of *Lactobacillus* strains in children with ongoing coeliac autoimmunity on a normal diet (FIGS. 1 and 2). This gives credible evidence of a dampening effect of probiotic supplements on early active coeliac autoimmunity never previously observed before. Only a gluten-free diet has been shown to reduce levels of tTG autoantibody efficiently over time (Agardh D, et al., *Acta paediatrica*. 2004; 93(8):1046-51). The effect of *Lactobacillus* on coeliac autoimmunity was further supported by the consistent changes in the peripheral immune response involved in the regulation of T cells, which was only observed in the children in the placebo group. Interestingly, the differences in most lymphocyte subsets found in the placebo group were similar to what is found in patients with active coeliac disease.

The increase of CD4+CD25+Foxp3+ T-cells in the placebo group, which remained unchanged in the treatment group, could be explained by the downregulation effects of the two *Lactobacillus* strains on activated CD4+ cells. The observed reduction in CD3+CD4+ cells in the placebo group may be considered to be secondary to the compartmentalization of gluten-sensitive lymphocytes within the intestinal mucosa. Furthermore, naïve T$_H$ cells expressing CD45RA were reduced meanwhile the percentage of effector and memory T$_H$ cells expressing CD45RO was higher in the placebo group, which has previously been observed in untreated celiac disease patients and explained by higher percentages of circulating CD45+αβTcR+ and γδTcR+ lymphocytes activated by gluten (Kerttula T O, et al., *Clin Exp Immunol*. 1998; 111(3):536-40). This explanation is further strengthened by the finding of an increased percentage of CD45RO+ cells also expressing CCR4 in the placebo group, suggesting a re-circulation of primed regulatory T-cells. CCR4 is an important chemokine receptor for recruitment of T-cells to the sight of inflammation and it is highly expressed on differentiated regulatory T cells (Iellem A, et al., *Eur J Immunol*. 2003; 33(6):1488-96). The increases of CD4+CD25$^{high}$CD45RO+CCR4+ cells and CD4+CD25+Foxp3+ cells in the placebo group indicate an attempt to extinguish an ongoing intestinal inflammation and the immune response to dietary gluten antigens as previously described (Frisullo G, et al., *Human Immunol*. 2009; 70(6):430-5; Tiittanen M, et al., *Clin Exp Immunol*. 2008; 152(3):498-507).

The third finding of particular relevance was the peripheral changes in NK cells over time in the placebo group with ongoing coeliac autoimmunity, which was not observed in children that received probiotics. The population of NK and NK-T cells has been found to decrease in both tissue and in periphery in active coeliac disease (Dunne M R, et al., *PLoS ONE*. 2013; 8(10):e76008). This is in line with the findings of our study, where we found that NK cells increased in the probiotic group, but not in the placebo group. This further supports the importance of NK cells in coeliac disease and that the probiotic supplement may have a direct or indirect stimulatory effect on NK cells mirrored as a reduced autoimmune response in the periphery.

CONCLUSIONS

To summarise, by comparing immune profiles between the groups, we were able to identify a distinct suppressing effect on coeliac autoimmunity mirrored as a decrease in levels of tTG autoantibodies. This observation was further strengthened by the consistent changes of peripheral changes in the proportions of T lymphocytes involved in autoimmune regulation and NK cells notably seen in children with ongoing coeliac autoimmunity that received placebo. This novel finding offers a potential new field of therapeutic intervention with probiotic bacteria in human autoimmune disease.

We chose to study the immunological changes associated with CD pathology without the influence of GFD. Treatment with a GFD causes a rapid change in several immunological markers such as tTGA in CD patients. (Midhagen G, et al., Journal of Internal Medicine. 2004; 256(6):519-24) and (Agardh D, et al., Clinical and Experimental Immunology. 2006; 144(1):67-75). Consequently, we utilized a low cut-off limit of <30 U/ml for study participation, in accordance to current diagnostic guidelines stating that significantly elevated tTGA levels can be sufficient evidence to make a diagnosis of CD without an intestinal biopsy (Husby S, et al., *Journal of Pediatric Gastroenterology and Nutrition*. 2012; 54(1):136-60 The fact that a majority of our participants entered the study with low initial tTGA levels as an early sign of ongoing autoimmunity was therefore expected and an inherent component of our population.

While both IgA-tTGA and IgG-tTGA levels are valid diagnostic tests in CD, the current clinical recommendations advocate the use of IgA-tTGA in children with normal total IgA levels, due to a higher specificity and clinical relevance (Husby S, et al., supra).

In this study, changes in IgA-tTGA levels in the probiotic Lactobacilli-treated group were reduced more significantly than the placebo group. Indeed, this was reflected by two children treated with Lactobacilli that progressed to high levels from invitation to visit 0 that significantly reduced their IgA-tTGA levels after 3 and 6 months, indicating that probiotics may have had an effect in some children with CD autoimmunity (data not shown).

The exemplary probiotic Lactobacilli used in this clinical study, *Lactobacillus plantarum* HEAL9 and *Lactobacillus paracasei* 8700:2, showed suppressing effects on CD autoimmunity in children on a gluten-containing diet. This indicated that *Lactobacillus* strains can prevent and/or delay CD autoimmunity in 'at HLA-risk' individuals, suggesting a possible preventive application of probiotic Lactobacilli in CD.

To our knowledge, this is the first interventional study to evaluate and show that probiotic Lactobacilli species may delay or prevent the development of ongoing CD autoimmunity in children at genetic risk for CD. It indicates that the probiotic *Lactobacillus* strains of the invention can be used to delay and/or prevent progression from CDA to CD.

The invention claimed is:

1. A method of treating and/or preventing celiac disease autoimmunity (CDA) or celiac disease (CD) in a subject, said method comprising administering to the subject an effective amount of a combination of *Lactobacillus paracasei* strain DSM 13434(8700:2) and *Lactobacillus plantarum* strain DSM 15312 (HEAL9).

2. The method of claim 1, wherein the combination of strains is administered in a total amount of from $1 \times 10^6$ to $1 \times 10^{14}$ CFU per daily dose.

3. The method of claim 1, comprising administering to the subject a composition containing said combination of strains together with a suitable excipient or carrier.

4. The method of claim 3, wherein the carrier is a food and/or a micronutrient.

5. The method of claim 3, wherein the composition is provided as a capsule, tablet or powder for oral administration.

6. The method of claim 1, wherein said combination of strains is in the form of a freeze-dried preparation.

7. The method of claim 1, wherein the subject is a human identifiable as being at an increased risk of CD by the presence of one or more serological, immunological and/or genetic risk factors.

8. The method of claim 7 wherein the genetic risk factor is HLA-DQ2 and/or HLA-DQ8.

9. The method of claim 7, wherein the immunological risk factor is persistent tissue transglutaminase (tTGA) positivity.

10. The method of claim 1, wherein the effective amount of said combination of strains is a total amount of $1 \times 10^{10}$ CFU per daily dose.

11. The method of claim 1, where the method (a) reduces the severity, and/or (b) removes one or more symptoms and/or markers associated with CDA or CD.

12. A method of reducing the severity and/or removing one or more symptoms and/or markers associated with celiac disease autoimmunity (CDA) or celiac disease (CD) in a subject, said method comprising administering to the subject an effective amount of a combination of *Lactobacillus paracasei* strain DSM 13434 (8700.2) and *Lactobacillus plantarum* strain DSM 15312 (HEAL9).

* * * * *